US00RE38090E

(19) United States
(12) Reissued Patent
Matsuda et al.

(10) Patent Number: US RE38,090 E
(45) Date of Reissued Patent: Apr. 22, 2003

(54) 3'-SUBSTITUTED NUCLEOSIDE DERIVATIVE

(75) Inventors: Akira Matsuda, 1-7-501, Kita-24-jo, Nishi-12-chome, Kita-ku, Sapporo-shi Hokkaido 001 (JP); Takuma Sasaki, 12-5-401, Izumino-machi 4-chome, Kanazawa-shi Ishikawa 921 (JP)

(73) Assignees: Akira Matsuda, Hokkaido (JP); Takuma Sasaki, Ishikawa (JP); Taiho Pharmaceutical Co., Ltd., Tokyo (JP)

(21) Appl. No.: 09/584,171

(22) PCT Filed: Dec. 13, 1995

(86) PCT No.: PCT/JP95/02554

§ 371 (c)(1),
(2), (4) Date: Aug. 13, 1996

(87) PCT Pub. No.: WO96/18636

PCT Pub. Date: Jun. 20, 1996

Related U.S. Patent Documents

Reissue of:
(64) Patent No.: 5,763,418
Issued: Jun. 9, 1998
Appl. No.: 08/693,161
Filed: Aug. 13, 1996

(30) Foreign Application Priority Data

Dec. 13, 1994 (JP) ..... 6-308912
Aug. 16, 1995 (JP) ..... 7-208645

(51) Int. Cl.[7] ..... A61K 31/70; C07H 19/04

(52) U.S. Cl. ..... 514/45; 514/46; 514/47; 514/48; 514/49; 514/50; 514/51; 536/26.23; 536/26.26; 536/26.7; 536/26.71; 536/26.74; 536/26.8; 536/27.11; 536/27.6; 536/27.62; 536/27.63; 536/27.8; 536/27.81; 536/28.5; 536/28.51; 536/28.52; 536/28.53; 536/28.54; 536/28.55

(58) Field of Search ..... 514/45–51; 536/26.23, 536/26.26–26.7, 26.71, 26.74, 26.8, 27.11, 27.6, 27.62, 27.63, 27.8, 27.81, 28.5–28.55

(56) References Cited

U.S. PATENT DOCUMENTS 5,681,940 A * 10/1997 Wang et al. ..... 536/22.1
5,763,418 A * 6/1998 Matsuda et al. ..... 514/45

FOREIGN PATENT DOCUMENTS

| | | | |
|---|---|---|---|
| DE | 3924424 | * | 1/1991 |
| DE | 4204032 | * | 8/1993 |
| DE | 1950038 | * | 9/1996 |
| WO | 9318051 | * | 9/1993 |
| WO | 9532984 | * | 12/1995 |
| WO | 9614329 | * | 5/1996 |

OTHER PUBLICATIONS

Alvarez et al., "Novel TSAO Derivatives, Synthesis and Anti–HIV–1 Activity of Allofuranosyl–TSAO–T Analogues," *Nucleosides & Nucleotides*, 15(1–3), 349–359 (Jan.–Mar., 1996).*

Matsuda et al. (II), "Nucleosides and Nucleotides. 152. 1–(3–C–Ethynyl–β–D–Ribo–pentofuranosyl)uracil as a Broad Spectrum Antitumor Nucleoside," *Bioorganic Medicinal Chemistry Letters*, 6(16), 1887–1892 (Aug. 20, 1996).*

Johnson et al., "3'–C–Trifluoromethyl Ribonucleosides," *Nucleosides & Nucleotides*, 14(1&2), 185–194 (Feb.–Apr., 1995).*

Ichikawa et al., "Nucleosides and Nucleotides. 163. Synthesis of 3'–β–Branched Uridine Derivatives via Intramolecular Reformatsky–Type Reaction Promoted by Samarium Diiodide," *Journal of Organic Chemistry*, 62(5), 1368–1375 (Mar. 7, 1997).*

Nielson et al., "Stereoselective Synthesis of 3'–Allyluridines and 3'–Spiro–γ–lactone Uridine Analogues," *Acta Chemica Scandinavica*, 30(11), 1030–1035 (Nov., 1996).*

Jung et al., "Rapid and Efficient Stereocontrolled Synthesis of C–3'–Ethynyl Ribo and Xylonucleosides by Organocerium Additions to 3'–Ketonucleosides," *Tetrahedron Letters*, 36(7), 1031–1034 (Feb. 13, 1995).*

Beigelman et al., "Efficient Epimerization in the Acetolysis of 3–O–Acetyl–5–O–benzoyl–1, 2–O–isopropylidene–3–C–methylnucleosides with β–D–Ribo– and α–D–Arabino–Configurations," *Doklady Chemistry*(Engish Translation), 296(4–6), 458–461 (Apr., 1988); *Doklady Akademii Nauk SSSR Chem. Sec.*, (Russian), 296(4–6), 1379–1382 (Oct., 1987).*

Huss et al., "Synthesis of 3'–Ethynylnucleosides of Thymine," *Tetrahedron*, 47(9), 1727–1736 (Feb. 25, 1991).*

Shimamoto et al., "Antitumor Activity and Pharmacokinetics of TAS–106, 1–(3–C–Ethynyl–β–D–ribopentofuranosylcytosine," *Japanese Journal of Cancer Research*, 92, 343–351 (Mar., 2001).*

* cited by examiner

*Primary Examiner*—James O. Wilson
*Assistant Examiner*—L E Crane
(74) *Attorney, Agent, or Firm*—Sughrue Mion, PLLC

(57) ABSTRACT

The invention relates to a 3'-substituted nucleoside derivative represented by the following general formula (1):

(1)

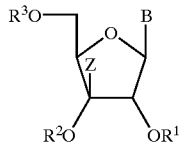

wherein B means a nucleic acid base which may have a substituent, Z represents a lower alkynyl or lower alkenyl group which may be substituted by a group represented by the formula:

(2)

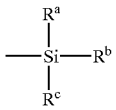

in which $R^a$, $R^b$ and $R^c$ are individually a lower alkyl group or a phenyl group, or an oxiranyl group which may have at least one lower alkyl group, $R^1$ and $R^2$ individually represent H or an ester-forming residue capable of easily leaving in a living body, and $R^3$ is H, a mono- or polyphosphoric acid residue, or an ester-forming residue capable of easily leaving in a living body, with the proviso that the sugar moiety is ribose, or a pharmaceutically acceptable salt thereof. The 3'-substituted nucleoside derivative according to the invention has an excellent antitumor activity and is hence useful for treatment for and prevention of cancers.

22 Claims, No Drawings

3'-SUBSTITUTED NUCLEOSIDE DERIVATIVE

Matter enclosed in heavy brackets [ ] appears in the original patent but forms no part of this reissue specification; matter printed in italics indicates the additions made by reissue.

*CROSS-REFERENCE TO RELATED APPLICATIONS*

*This application is a Reissue of U.S. Pat. No. 5,763,418, which issued from U.S. application Ser. No. 08/693,161, filed Apr. 13, 1996; which is a National stage filing under 35 U.S.C. §371 of PCT/JP95/02554, filed Dec. 13, 1995.*

TECHNICAL FIELD

The present invention relates to a new nucleic acid derivative, and more particularly to a 3'-substituted nucleoside derivative or a pharmaceutically acceptable salt thereof, which has excellent antitumor activities and is useful as a medicine such as an antitumor agent, and use of such a compound for a medicine.

BACKGROUND ART

Pyrimidine compounds such as 5-fluorouracil, tegafur, UFT, doxifluridine, carmofur, cytarabine and enocitabine have heretofore been known as antitumor agents which are nucleic acid antimetabolites.

On the other hand, 1-(2-O-(tert-butyldimethylsilyl)-3-C-ethynyl-β-D-ribofuranosyl)thymine has been known as a pyrimidine or purine nucleoside having an alkynyl group at a 3-position of a sugar moiety from Tetrahedron, 47, 1727–1736 (1991). There is however no description as to the medicinal utility of this compound, in particular, antitumor action. 1-(3-C-Ethynyl-β-D-xylofuranosyl)thymine and 1-(2-O-(tert-butyldimethylsilyl)-3-C-ethynyl-β-D-xylofuranosyl)thymine are also described ibid. The sugar moieties of these two compounds are both composed of xylose and differ in the configuration at a 3-position from the ribose in the compounds according to the present invention. Besides, the literature does not describe anything about antitumor action. compounds having an alkyl group at a 3-position of a sugar moiety are described in Japanese Patent Publication Nos. 11908/1970 and 4376/1971. However, their antitumor effects are extremely little, and they are hence of no utility value as anticancer agents under circumstances.

Accordingly, it is an object of the present invention to provide a new nucleic acid derivative which has excellent antitumor activities and is useful as a medicine, and a medicine comprising such a compound.

In view of the foregoing circumstances, the present inventor has carried out an extensive investigation. As a result, it has been found that a nucleic acid derivative at a 3-position of the sugar moiety of which a substituent has been introduced has excellent antitumor activities and is useful as an antitumor agent, thus leading to completion of the present invention.

DISCLOSURE OF THE INVENTION

The present invention provides a 3'-substituted nucleoside derivative represented by the following general formula (1):

(1)

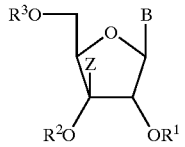

wherein B means a nucleic acid base which may have a substituent, Z represents a lower alkynyl or lower alkenyl group which may be substituted by a group represented by the general formula (2):

(2)

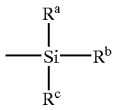

in which $R^a$, $R^b$ and $R^c$ may be the same or different from one another and individually represent a lower alkyl group or a phenyl group, or an oxiranyl group which may be substituted by at least one lower alkyl group, $R^1$ and $R^2$ individually represent a hydrogen atom or an ester-forming residue capable of easily leaving in a living body, and $R^3$ is a hydrogen atom, a mono- or polyphosphoric acid residue, or an ester-forming residue capable of easily leaving in a living body, with the proviso that the sugar moiety is ribose, or a pharmaceutically acceptable salt thereof.

The compound of the present invention represented by the general formula (1) has excellent antitumor activities and is useful as a medicine such as a remedy for various tumors.

Accordingly, the present invention also provides a medicinal composition comprising the compound of the general formula (1) or a pharmaceutically acceptable salt thereof and a pharmaceutical carrier.

The present invention further provides a medicine, in particular, an antitumor agent, comprising the compound of the general formula (1) or a pharmaceutically acceptable salt thereof as an active ingredient.

The present invention further provides use of the compound of the general formula (1) or a pharmaceutically acceptable salt thereof for a medicine.

The present invention still further provides a method of treating or preventing a cancer of a mammal, which comprises administering an effective amount of the compound of the general formula (1) or a pharmaceutically acceptable salt thereof to the mammal.

The present invention yet still further provides a process for the preparation of the compound of the general formula (1) or a pharmaceutically acceptable salt thereof.

BEST MODE FOR CARRYING OUT THE INVENTION

Examples of the nucleic acid residue represented by B in the general formula (1) include pyrimidine bases such as cytosine, thymine and uracil, and purine bases such as adenine and guanine.

Examples of the substituent, by which the nucleic acid base may be substituted, include halogen atoms, lower alkyl groups, acyl groups such as aliphatic acyl groups or aromatic acyl groups, and substituted oxycarbonyl groups such as lower alkoxycarbonyl groups, lower alkenyloxycarbonyl groups or aralkyloxycarbonyl groups.

Examples of the halogen atoms include fluorine, chlorine, bromine and iodine atoms.

Examples of the lower alkyl groups include linear or branched alkyl groups having 1–6 carbon atoms, such as methyl, ethyl, n-propyl, isopropyl, n-butyl, isobutyl, sec-butyl, tert-butyl, pentyl and hexyl groups.

Examples of the aliphatic acyl groups include linear or branched acyl groups having 1–6 carbon atoms, such as formyl, acetyl, propionyl, butyryl, isobutyryl, pentanoyl and hexanoyl groups. Examples of the aromatic acyl groups include benzoyl, α-naphthoyl and β-naphthoyl. These groups may also have a lower alkyl group, lower alkoxy group, halogen atom, nitro group or the like as a substituent.

As examples of the lower alkyl group and halogen atom, may be mentioned the same groups and atoms as those mentioned above.

Examples of the lower alkoxy group include linear or branched alkoxy groups having 1–6 carbon atoms, such as methoxy, ethoxy, n-propoxy, isopropoxy, n-butoxy, isobutoxy, sec-butoxy, tert-butoxy, pentyloxy and hexyloxy groups.

Examples of the lower alkoxycarbonyl groups include linear or branched alkoxycarbonyl groups having 2–7 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl and hexyloxycarbonyl groups.

Examples of the lower alkenyloxycarbonyl groups include linear or branched alkenyloxycarbonyl groups having 3–7 carbon atoms, such as vinyloxycarbonyl, allyloxycarbonyl, isopropenyloxycarbonyl, 1-butenyloxycarbonyl and 2-butenyloxycarbonyl groups.

Examples of the aralkyloxycarbonyl groups include aralkyloxycarbonyl groups having 8–12 carbon atoms, such as benzyloxycarbonyl, phenethyloxycarbonyl, α-naphthylmethyloxycarbonyl and β-naphthylmethyloxycarbonyl groups. These groups may have a lower alkyl group, lower alkoxy group, halogen atom, nitro group or the like as a substituent.

Examples of the lower alkynyl group represented by Z include alkynyl groups having 2–6 carbon atoms, such as ethynyl, propynyl (1-propynyl, 2-propynyl), butynyl (1-butynyl, 2-butynyl, etc.), pentynyl (1-pentynyl, etc.) and hexynyl (1-hexynyl, etc.) groups, while examples of the lower alkenyl group include alkenyl groups having 2–6 carbon atoms, such as ethenyl, propenyl (1-propenyl, 2-propenyl, isopropenyl), butenyl (1-butenyl, 2-butenyl, 3-butenyl, etc.), pentenyl (1-pentenyl, etc.) and hexenyl (1-hexenyl, etc.) groups. Examples of the oxiranyl group having at least one lower alkyl group include oxiranyl groups substituted by one or two lower alkyl groups, such as 3-methyloxiranyl, 3-ethyloxiranyl, 3-propyloxiranyl, 3-isopropyloxiranyl, 3-butyloxiranyl, 3-tert-butyloxiranyl, 3,3-dimethyloxiranyl and 3,3-diethyloxiranyl groups.

Examples of the group represented by the general formula (2) include silyl groups substituted by three linear or branched alkyl groups having 1–6 carbon atoms, such as trimethylsilyl, triethylsilyl, tripropylsilyl, triisopropylsilyl, tri-tert-butylsilyl, trihexylsilyl, dimethylethylsilyl, dimethylisopropylsilyl, diethylisopropylsilyl, diisopropylmethylsilyl, di-tert-butylmethylsilyl and tert-butyldimethylsilyl groups, and diphenylmethylsilyl, dimethylphenylsilyl, tert-butyldiphenylsilyl and triphenylsilyl groups.

The ester-forming residues capable of easily leaving in a living body, which are represented by $R^1$, $R^2$ and $R^3$, mean nontoxic ester residues which easily cleave in the blood and tissue of mammals including the human to release their corresponding hydroxyl compounds (namely, compounds in which $R^1$, $R^2$ and/or $R^3$ turns to a hydrogen atom). No limitation is imposed on the ester-forming residue so far as it is generally well-known, protects the hydroxyl groups of the nucleoside and forms an ester. Examples thereof include acyl groups such as aliphatic acyl groups which may have a substituent and aromatic acyl groups which may have a substituent, lower alkylcarbamoyl groups, and amino acid residues.

Examples of the aliphatic or aromatic acyl groups which may have a substituent include lower alkanoyl groups, arylcarbonyl groups, heterocyclic carbonyl groups, aryloxycarbonyl groups, lower alkoxycarbonyl groups and acyloxyacyl groups.

Examples of the lower alkanoyl groups include alkanoyl groups which may have a halogen atom, lower alkoxy group or the like as at least one substituent and have 1–6 carbon atoms, such as formyl, acetyl, propionyl, butyryl, isobutyryl, pentanoyl, hexanoyl, chloroacetyl, dichloroacetyl, trichloroacetyl, trifluoroacetyl, methoxyacetyl and ethoxyacetyl groups.

Example of the arylcarbonyl groups include benzoyl and naphthylcarbonyl groups which may have a lower alkyl group, lower alkoxy group, halogen atom, carboxyl group, nitro group, cyano group and the like as at least one substituent, such as benzoyl, α-naphthylcarbonyl, β-naphthylcarbonyl, 2-methylbenzoyl, 3-methylbenzoyl, 4-methylbenzoyl, 2,4-dimethylbenzoyl, 4-ethylbenzoyl, 2-methoxybenzoyl, 3-methoxybenzoyl, 4-methoxybenzoyl, 2,4-dimethoxybenzoyl, 4-ethoxybenzoyl, 2-methoxy-4-ethoxybenzoyl, 4-propoxybenzoyl., 2-chlorobenzoyl, 3-chlorobenzoyl, 4-chlorobenzoyl., 2,3-dichlorobenzoyl, 2-bromobenzoyl, 4-fluorobenzoyl, 2-carboxybenzoyl, 3-carboxybenzoyl, 4-carboxybenzoyl, 2-cyanobenzoyl, 4-cyanobenzoyl, 2-nitrobenzoyl, 4-nitrobenzoyl and 2,4-dinitrobenzoyl groups.

Examples of the heterocyclic carbonyl groups include 2-furanylcarbonyl, 4-thiazolylcarbonyl, 2-quinolylcarbonyl, 2-pyrazinylcarbonyl, 2-pyridylcarbonyl, 3-pyridylcarbonyl and 4-pyridylcarbonyl groups.

Examples of the aryloxycarbonyl groups include phenoxycarbonyl, α-naphthyloxycarbonyl, β-naphthyloxycarbonyl, 2-methylphenoxycarbonyl, 3-methylphenoxycarbonyl, 4-methylphenoxycarbonyl, 2,4-dimethylphenoxycarbonyl, 4-ethylphenoxycarbonyl, 2-methoxyphenoxycarbonyl, 3-methoxyphenoxycarbonyl, 4-methoxyphenoxycarbonyl, 2,4-dimethoxyphenoxycarbonyl, 4-ethoxyphenoxycarboxy, 2-methoxy-4-ethoxyphenoxycarbonyl, 2-chlorophenoxycarbonyl, 3-chlorophenoxycarbonyl, 4-chlorophenoxycarbonyl, 2,3-dichlorophenoxycarbonyl, 2-bromophenoxycarbonyl, 4-fluorophenoxycarbonyl, β-methyl-α-naphthyloxycarbonyl, and β-chloro-α-naphthyloxycarbonyl groups.

Examples of the lower alkoxycarbonyl groups include alkoxycarbonyl groups having 2–6 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and pentyloxycarbonyl groups.

Examples of the acyloxyacyl groups include acetyloxyacetyl, propionyloxyacetyl and α-(acetyloxy) propionyl, β-(propionyloxy)propionyl groups.

Examples of the lower alkylcarbamoyl groups include carbamoyl groups mono- or disubstituted by lower alkyl groups having 1–6 carbon atoms, such as methylcarbamoyl, ethylcarbamoyl, propylcarbamoyl, butylcarbamoyl, penthylcarbamoyl, hexylcarbamoyl, dimethylcarbamoyl and diethylcarbamoyl groups.

The amino acid residues mean groups which are formed by removing a hydroxyl group from a carboxyl group of an amino acid and may be derived from both natural and synthetic amino acids. Examples of such amino acids include glycine, alanine, β-alanine, valine and isoleucine. However, any amino acid residues may be included so far as they are amino acid residues described in Japanese Patent Application Laid-Open No. 104093/1989.

As other ester-forming residues, any of general ester-forming residues described in, for examples, THEODORA W. GREENE, "PROTECTIVE GROUPS IN ORGANIC SYNTHESIS Second Edition", JOHN WILEY & SONS, INC. (1991); <Shin Jikken Kagaku Koza 4 (New Experimental Chemistry Course 4)> edited by The Chemical Society of Japan, "Synthesis and Reaction of Organic Compounds (V)" Chapter 11, pp. 2495, Maruzen (198:3); and Japanese Patent Application Laid-Open Nos. 106593/1986, 149696/1987 and 153696/1989 and conventionally used as ester-forming residues may be mentioned.

Examples of the mono- or polyphosphoric acid residue represented by $R^3$ include monophosphate, diphosphate and triphosphate groups and hydroxyl group-protected radicals thereof. Examples of protecting groups include lower alkyl groups which may be substituted by a halogen atom or a cyano group, a benzyl group which may have a substituent, and a phenyl group which may have a substituent. Further, this residue may be a 3',5-cyclic phosphate group which forms a cyclic structure with the nucleic acid base.

Preferable examples of B include cytosine, thymine, uracil, adenine, guanine, 5-fluorocytosine, 5-fluorouracil, $N^6$-benzoyladenine, $N^2$-acetylguanine and 2-chloroadenine. More preferable examples thereof include cytosine, uracil, adenine, 5-fluorocytosine and 5-fluorouracil.

Preferable examples of Z include lower alkynyl or lower alkenyl groups which may be substituted by a group represented by the general formula (2). More preferable examples thereof include ethynyl, propynyl, butynyl, ethenyl, trimethylsilylethynyl, triethylsilylethynyl, triisopropylsilylethynyl and triphenylsilylethynyl groups. Particularly preferable examples thereof include ethynyl and trimethylsilylethynyl groups.

A preferable example of $R^1$ and $R^2$ includes a hydrogen atom.

Preferable examples of $R^3$ include a hydrogen atom and mono- and polyphosphoric acid residues. More preferable examples thereof include a hydrogen atom and a diphosphate group.

Preferable examples of the ester-forming residues capable of easily leaving in a living body represented by $R^1$, $R^2$, $R^3$ include acyl groups. More preferable examples thereof include acetyl and benzoyl groups.

The preferable compounds according to the present invention are 3'-substituted nucleoside derivatives in which B in the general formula (1) is cytosine, thymine, uracil, adenine, guanine, 5-fluorocytosine, 5-fluorouracil, $N^6$-benzoyladenine, $N^2$-acetylguanine or 2-chloroadenine, Z is a lower alkynyl or lower alkenyl group which may be substituted by a group represented by the general formula (2), $R^1$ and $R^2$ are hydrogen atoms, and $R^3$ is a hydrogen atom or a mono- or polyphosphoric acid residue.

More preferable compounds are 3'-substituted nucleoside derivatives in which B in the general formula (1) is cytosine, uracil, adenine, 5-fluorocytosine or 5-fluorouracil, Z is an ethynyl, propynyl, butynyl, ethenyl, trimethylsilylethynyl, triethylsilylethynyl, triisopropylsilylethynyl or triphenylsilylethynyl group, $R^1$ and $R^2$ are hydrogen atoms, and $R^3$ is a hydrogen atom or a diphosphate group.

Particularly preferable compounds are 3'-substituted nucleoside derivatives in which B in the general formula (1) is cytosine or uracil, Z is an ethynyl or trimethylsilylethynyl group, and $R^1$, $R^2$ and $R^3$ are hydrogen atoms.

The compounds according to the present invention also include those being in the form of a salt. No particular limitation is imposed on such salts so far as they are pharmaceutically acceptable salts. For example, in the case where $R^3$ is a hydrogen atom, acid-added salts, such as inorganic acid salts such as hydrochlorates, hydrobromates and sulfates; and organic acid salts such as organic sulfonates such as methanesulfonates and benzenesulfonates, and aliphatic carboxylic acid salts such as acetates, propionates and trifluoroacetates may be exemplified. In the case where $R^3$ is a mono- or polyphosphoric acid residue, alkali metal salts such as sodium, potassium and lithium salts, alkaline earth metal salts such as calcium salts, and ammonium salts may be exemplified. The compounds according to the present invention further include hydrates thereof.

The compounds according to the present invention represented by the general formula (1) can be prepared in accordance with, for example, the following reaction scheme 1 or 2.

Reaction Scheme 1:

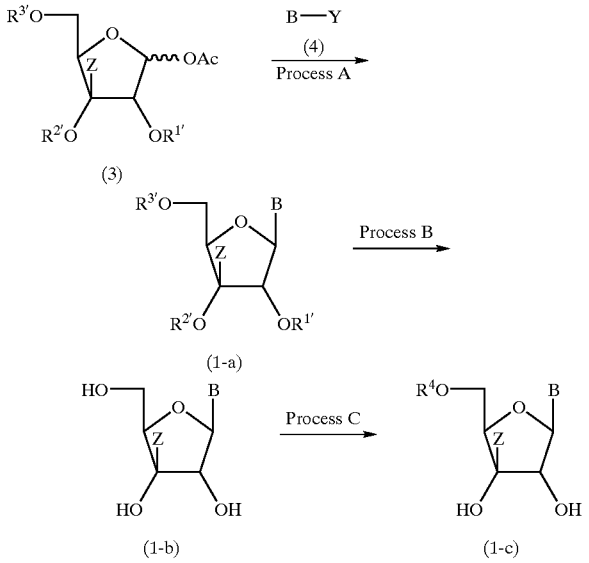

wherein B and Z have the same meaning as defined above, $R^{1'}$, $R^{2'}$ and $R^{3'}$ denote individually a protecting group for a hydroxyl group, Y means a silyl protecting group, and $R^4$ stands for a hydrogen atom or a mono- or polyphosphoric acid residue.

No limitation is imposed on the protecting groups for the hydroxyl groups represented by $R^{1'}$, $R^{2'}$ and $R^{3'}$ so far as they may be used as usual protecting groups for nucleosides. Examples thereof include acyl groups such as aliphatic acyl groups which may have a substituent and aromatic acyl groups which may have a substituent, lower alkoxycarbonyl groups, lower alkylcarbamoyl groups, lower alkyl groups, arylalkyl groups, silyl protecting groups, and amino acid residues.

As the acyl groups such as aliphatic acyl groups or aromatic acyl groups, the lower alkoxycarbonyl groups, the lower alkylcarbamoyl groups and the amino acid residues, there may be used those described above. As the lower alkyl groups, those described above may be used, while alkyl groups having a halogen atom, lower alkoxy group or the like as a substituent, such as chloromethyl, methoxymethyl, ethoxymethyl, methoxyethyl and ethoxyethyl groups, may be included.

Examples of the arylalkyl groups include benzyl, benzhydryl and trityl groups. These groups may have a lower alkyl group, lower alkoxy group, halogen atom, nitro group or the like as a substituent.

Examples of the silyl protecting groups include trimethylsilyl, tert-butyldimethylsilyl, methyldiisopropylsilyl, triisopropylsilyl and tetraisopropyldisiloxyl (TIPDS). The same may be said of the silyl protecting group represented by Y.

(Process A)

A compound represented by the general formula (3) is reacted with a silylated nucleic acid base represented by the general formula (4), thereby obtaining a compound of the present invention represented by the general formula (1-a).

The compound represented by the general formula (3) is a known compound or obtained in accordance with any known method. More specifically, the compound can be prepared in accordance with Reaction Scheme 3 which will be described subsequently.

The silylated nucleic acid base represented by the general formula (4) is a known compound or obtained in accordance with any known method. In general, the compound can be obtained by using, for example, the method disclosed by vorbruggen et al. (Chem. Ber. 114, 1234 (1981)). More specifically, a suspension is prepared from a nucleic acid base and a silylating agent such as hexamethyldisilazane. Trimethylsilyl chloride is further added to the suspension as needed, and the mixture is heated under reflux in an argon atmosphere, thereby obtaining the intended compound.

The reaction of Process A is conducted in the presence of a Lewis acid in a nonpolar solvent.

No particular limitation is imposed on the Lewis acid. However, examples thereof include trimethylsilyl trifluoromethanesulfonate, tin tetrachloride and titanium tetrachloride. As the nonpolar solvent, any solvent may be used so far as it does not participate in the reaction. Examples thereof include chloroform, dichloromethane, dichloroethane and acetonitrile.

With respect to the proportions of the reactants in the reaction, it is preferable to use the compound of the general formula (4) and the Lewis acid in proportions of 1–10 moles, preferably 1–5 moles, and 1–10 moles, preferably 1–5 moles, respectively, per mole of the compound of the general formula (3). With respect to the reaction temperature, the Lewis acid is added at 0° C., and the reaction is conducted at 0°–100° C., preferably a temperature near room temperature. With respect to the reaction time, the reaction favorably progresses in 0.1–50 hours, preferably 1–24 hours.

(Process B)

In order to remove the protecting groups of the compound represented by the general formula (1-a) obtained in Process A, methods commonly used for the protecting groups used, for example, acid hydrolysis, alkaline hydrolysis, ammonium treatment and catalytic reduction may be suitably used. A compound of the present invention represented by the general formula (1-b) can be obtained by hydrolyzing the compound (1-a) with an alkali such as sodium hydroxide, potassium hydroxide or an ammonium derivative in a lower alcohol, for example, methanol in the case where the protecting groups are acyl groups by way of example, or by treating the compound (1-a) with an ammonium fluoride derivative in the case where the protecting groups are silyl groups.

With respect to the proportions of the reactants in the reaction, it is preferable to use the basic compound in a catalytic amount based on the compound represented by the general formula (1-a) in the case where the protecting groups are acyl groups. The reaction temperature is 0°–150° C., preferably room temperature to 100° C. With respect to the reaction time, the reaction favorably progresses in 0.1–100 hours, preferably 1–60 hours.

(Process C)

The compound represented by the general formula (1-b) obtained in Process B is phosphorylated with a phosphorylating agent in the presence of a solvent or without any solvent, thereby obtaining a compound according to the present invention represented by the general formula (1-c). Examples of the phosphorylating agent include phosphorylating agents generally used in selective phosphorylation of nucleosides at a 5'-position, such as phosphorus oxyhalides such as phosphorus oxychloride and phosphorus oxybromide, anhydrous phosphoric acids such as pyrophosphoric acid and polyphosphoric acid, phosphoric acid, phosphoric monoesters such as p-nitrophenyl phosphate, tetrachloropyrophosphoric acid, and trialkylammonium pyrophosphates. Of these, phosphorus oxychloride and tributylammonium pyrophosphate are preferred. As the solvent, any solvent may be used so far as it does not participate in the reaction. Examples thereof include pyridine, hexamethylphosphoric triamide, tetrahydrofuran, dioxane, acetonitrile, dimethylformamide, dichloromethane, chloroform, benzene, toluene, trimethyl phosphate and triethyl phosphate. The proportion of the phosphorylating agent used in the reaction is preferably 1–5 moles per mole of the compound of the general formula (1-b). The reaction temperature is −80° C. to 100° C., preferably −2020 C. to 50° C. With respect to the reaction time, in general, the reaction favorably progresses in about 0.5–12 hours.

Incidentally, upon the phosphorylation, 1,1'-carbonyldiimidazole, tetrazole, 1,2,4-triazole derivative or the like may be used as a reaction accelerator.

Reaction Scheme 2:

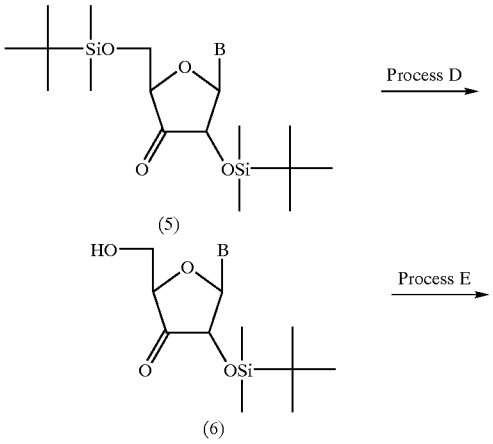

-continued

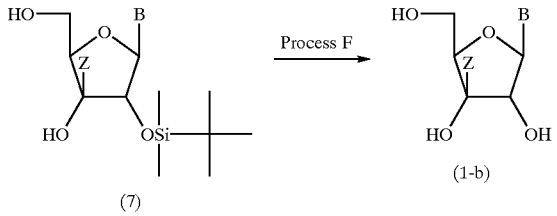

wherein B and Z have the same meaning as defined above.

(Process D)

A compound represented by the general formula (5) is partially hydrolyzed in accordance with, for example, the method described in J. Org. Chem., 55, 410–412 (1990), namely, by reacting the compound (5) at 0° C. in a mixture of trifluoroacetic acid-water, thereby conducting selective desilylation at a 5'-position to obtain a compound represented by the general formula (6).

The compound represented by the general formula (5) is a known compound or obtained in accordance with any known method, for example, the method described in J. Org. Chem. as described above; SYNTHESIS, 283–288 (1991); or Tetrahedron, 47, 1727–1736 (1991).

(Process E)

A substituent represented by Z is introduced in a 3-position of the compound represented by the general formula (6) to obtain a compound represented by the general formula (7). This reaction process can be performed in accordance with, for example, 1) a method in which a compound (which may be gaseous) represented by ZH or a complex of cerium chloride and ZH is reacted with the compound (6) in the presence of n-butyllithium in tetrahydrofuran, or 2) a method in which a Grignard reagent (ZMgBr) is reacted with. the compound (6) in tetrahydrofuran.

With respect to the proportions of the reactants, it is preferable to use the reaction reagent (ZH) and n-butyllithium in proportions of 1–10 moles, preferably 1–5 moles, and 1–10 moles, preferably 1–5 moles, respectively, per mole of the compound of the general formula (6). In the case where cerium chloride is used, an amount of cerium chloride to be used is preferably almost equimolar to the reaction reagent. The reaction temperature is preferably kept at −70° C. or lower in the case of the method 1) in which n-butyllithium is used, or is −20° to 50° C., preferably −10° C. to 10° C. in the case of the method 2) in which the reaction is performed with the Grignard reagent. With respect to the reaction time, the reaction favorably progresses in 0.1–50 hours, preferably 1–24 hours.

(Process F)

The compound represented by the general formula (7) is hydrolyzed, for example, by reacting the compound (7) in hydrochloric acid-methanol, thereby obtaining a compound according to the present invention represented by the general formula (1-b).

The reaction temperature is 0°–100° C., preferably a temperature near room temperature. With respect to the reaction time, the reaction favorably progresses in 1–100 hours.

Besides, the compound represented by the general formula (1-b) obtained in this process is subjected to the same reaction as in Process C of Reaction Scheme 1, whereby a compound represented by the general formula (1-c) can also be obtained.

Ester-forming residues can be introduced into the hydroxyl groups at 2'-, 3'- and 5'-positions of the compounds of the general formula (1-b) obtained in accordance with Reaction Schemes 1 and 2, or in the hydroxyl groups at 2'- and 3'-positions of the compound of the general formula (1-c) in accordance with any conventionally-known process, for example, the process disclosed in the above-described "PROTECTIVE GROUPS IN ORGANIC SYNTHESIS Second Edition" or <Shin Jikken Kagaku Koza 4 (New Experimental Chemistry Course 4)> edited by The Chemical Society of Japan, "Synthesis and Reaction of Organic Compounds (V)" or the process described in Japanese Patent Application Laid-Open No. 152898/1983, 56996/1985, 106593/1986, 149696/1987 or 153696/1989, thereby deriving other compounds according to the present invention from these compounds.

The compounds according to the present invention obtained by the above reactions can be formed into salts by the conventionally known method, for example, a method in which they are reacted with any of the above-described inorganic or organic acids in a proper solvent. Examples of the solvent include water, methanol, ethanol, dichloromethane, tetrahydrofuran, ethyl acetate and hexane.

The reaction is preferably conducted at a temperature of 0°–50° C. Besides, the compounds according to the present invention obtained by the above reactions can be formed into salts by the conventionally known method, for example, a method in which they are reacted with a strong base such as an alkali metal or alkaline earth metal hydroxide such as sodium hydroxide or potassium hydroxide, or a strong base such as sodium methoxide, potassium methoxide or sodium hydroxide in a proper solvent.

The above-described raw compound (3) can be prepared in accordance with, for example, the following reaction scheme.

Reaction Scheme 3:

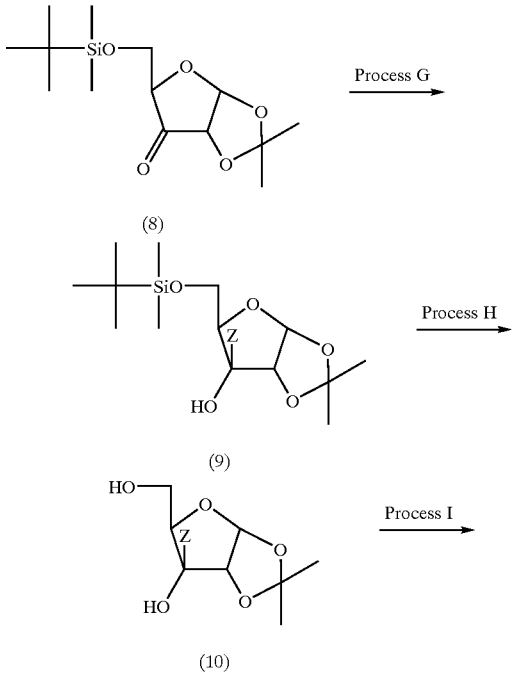

-continued

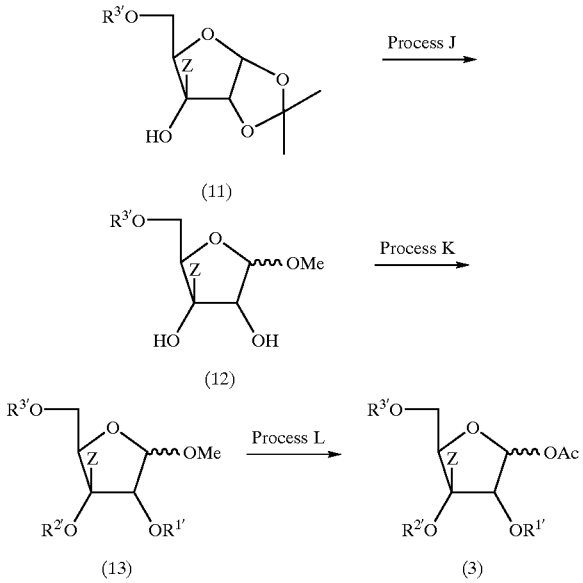

wherein Z, $R^{1'}$, $R^{2'}$ and $R^{3'}$ have the same meaning as defined above.

(Process G)

A known compound represented by the general formula (8) is reacted in the same manner as in Process E in the above Reaction Scheme 2, thereby obtaining a compound represented by the general formula (9).

(Process H)

The compound represented by the general formula (9) is reacted with tetrabutylammonium fluoride in tetrahydrofuran, thereby obtaining a compound represented by the general formula (10).

With respect to the proportions of the reactants in the reaction, it is preferable to use tetrabutylammonium fluoride in a proportion of 1–10 moles, preferably 1–5 moles per mole of the compound of the general formula (9). The reaction is conducted at a temperature of 0°–100° C., preferably a temperature near room temperature. With respect to the reaction time, the reaction favorably progresses in 0.1–2 hours, preferably 5–30 minutes.

(Process I)

The compound represented by the general formula (10) is reacted with a reactive substance, which protects a hydroxyl group, in a proper solvent, thereby obtaining a compound represented by the general formula (11).

As the solvent, any solvent may be used without any particular limitation so far as it does not participate in the reaction. In the case where a protecting group is an acyl group by way of example, it is only necessary to react an acylating agent such as an acid anhydride or acid halide in pyridine. Upon the reaction of this acylating agent, an amine such as dimethylaminopyridine or triethylamine may be added as a catalyst.

With respect to the proportions of the reactants in the reaction, it is preferable to use the reactive substance, which protects a hydroxyl group, in a proportion of 1–10 moles, preferably 1–5 moles per mole of the compound of the general formula (10). In the case where the catalyst is used, it is preferably used in a catalytic amount. The reaction is conducted at a temperature of −20° C. to 100° C., preferably a temperature near room temperature. With respect to the reaction time, the reaction favorably progresses in 0.1–10 hours, preferably 30 minutes to 5 hours.

(Process J)

The compound represented by the general formula (11) is subjected to acid alcoholysis, thereby obtaining a compound represented by the general formula (12).

As an alcohol, it is preferable to use a lower alcohol such as methanol or ethanol. A mixed solvent of the alcohol and water may be used.

Examples of an acid compound include carboxylic acids such as formic acid and acetic acid, acid anhydrides such as acetic anhydride, acid halides such as acetyl chloride, and inorganic acids such as hydrochloric acid, hydrobromic acid and sulfuric acid.

With respect to the proportions of the reactants in the reaction, it is preferable to use the acid compound in a proportion of 10–50 moles, preferably 20–40 moles per mole of the compound of the general formula (11). The reaction temperature is 0°–100° C., preferably a temperature near room temperature. With respect to the reaction time, the reaction favorably progresses in 1 minute to 10 hours, preferably 5 minutes to 5 hours.

(Process K)

The compound represented by the general formula (12) is reacted with a reactive substance, which protects a hydroxyl group, in a proper solvent, thereby obtaining a compound represented by the general formula (13).

As the solvent, any solvent may be used without any particular limitation so far as it does not participate in the reaction.

In the case where a protecting group is an acyl group by way of example, the compound (13) is obtained by reacting an acylating agent such as an acid anhydride or acid halide in pyridine. Upon the reaction of this acylating agent, an amine such as dimethylaminopyridine or triethylamine may be added as a catalyst.

With respect to the proportions of the reactants in the reaction, it is preferable to use the reactive substance, which protects a hydroxyl group, in a proportion of 1–20 moles, preferably 1–15 moles per mole of the compound of the general formula (12). In the case where the catalyst is used, it is preferably used in a catalytic amount, preferably a proportion of 1–5 moles per mole of the compound (12). The reaction temperature is 0° C. to 200° C., preferably room temperature to 150° C. With respect to the reaction time, the reaction favorably progresses in 0.1–50 hours, preferably 1–30 hours.

(Process L)

The compound represented by the general formula (13) is acetylated by adding concentrated sulfuric acid to the compound (13) in acetic acid and/or acetic anhydride, thereby obtaining the compound represented by the general. formula (3).

The reaction is conducted at a temperature of 0°–100° C. preferably a temperature near room temperature. With respect to the reaction time, the reaction favorably progresses in 0.1–24 hours, preferably 10 minutes to 5 hours.

The compounds according to the present invention obtained by the above reactions and the individual compounds can be isolated and purified by using conventionally-known separation and purification means, for example, concentration, solvent extraction, filtration, recrystallization, various chromatographies, etc.

From the compounds according to the present invention, medicinal compositions can be prepared by using suitable pharmaceutical carriers in accordance with a method known. per se in the art. As the carriers, there may be used various kinds of carriers routinely used in drugs, for example, excipients, binders, disintegrators, lubricants, colorants, flavors, smell corrigents, surfactants, etc.

No particular limitation is imposed on the dose form when the medicine or medicinal composition according to the present invention is used as a remedy for a tumor of mammals including the human. The form may be suitably selected according to the object of treatment. Specific examples of the form include parenteral preparations such as injections, suppositories, external preparations (ointments, plasters, etc.) and aerosol preparations, and oral preparations such as tablets, coated tablets, powders, granules, capsules, pills and solutions (suspensions, emulsions, etc.).

The various compositions described above are prepared in accordance with the preparation methods generally known in this field.

When the composition is prepared in the form of an injection, for example, a diluent such as water, ethyl alcohol, macrogol, propylene glycol, ethoxylated isostearyl alcohol, polyoxylated isostearyl alcohol or polyoxyethylene sorbitan fatty acid ester, a pH adjustor and a buffer such as sodium citrate, sodium acetate or sodium phosphate, a stabilizer such as sodium pyrosulfite, ethylenediaminetetra-acetic acid, thioglycolic acid or thiolactic acid, and the like may be used as carriers. In this case, sodium chloride, glucose or glycerol may be contained in the medicinal preparation in an amount sufficient to prepare an isotonic solution. Besides, conventional solubilizing aids, analgesics, local anesthetics and the like may also be added. These carriers can be added to prepare subcutaneous, intramuscular and intravenous injections in accordance with a method known per se in the art.

When the composition is prepared in the form of a suppository, polyethylene glycol, cacao butter, lanolin, higher alcohols, esters of higher alcohols, gelatin, semisynthetic glycerides, Witepsol (trade mark, product of Dynamit Nobel Co.) and the like may be used as carriers with a suitable absorbefacient added thereto.

When the composition is prepared in the form of ointments, for example, paste, cream and gel, a base, a stabilizer, a wetting agent, a preservative and the like, which are routinely used, are incorporated as needed, and the components are mixed to formulate the desired preparations in accordance with a method known per se in the art. As the base, there may be used, for example, white petrolatum, paraffin, glycerol, a cellulose derivative, polyethylene glycol, silicon or bentonite. As the preservative, methyl p-hydroxybenzoate, ethyl p-hydroxybenzoate, propyl p-hydroxybenzoate or the like may be used.

When the plaster is prepared, it is only necessary to apply the above ointment, cream, gel or paste to a support routinely used in a method known per se in the art. As the support, a fabric or nonwoven fabric made of cotton, rayon or chemical fibers, or a film or foamed sheet of soft polyvinyl chloride, polyethylene or polyurethane is suitable.

When the composition is prepared in the form of oral solid preparations such as tablets, powder and granules, there may be used, as carriers, excipients such as lactose, sucrose, sodium chloride, glucose, urea, starch, calcium carbonate, kaolin, crystalline cellulose, silicic acid methylcellulose, glycerol, sodium alginate and gum arabic; binders such as simple syrup, glucose solution, starch solution, gelatin solution, polyvinyl alcohol, polyvinyl ether, polyvinyl pyrrolidone, carboxymethylcellulose, shellac, methylcellulose, ethylcellulose, water, ethanol and potassium phosphate; disintegrators such as dry starch, sodium alginate, agar powder, laminaran powder, sodium bicarbonate, calcium carbonate, polyoxyethylene sorbitan fatty acid esters, sodium lauryl sulfate, stearic acid monoglyceride, starch and lactose; disintegration-preventing agents such as sucrose, stearic acid, cacao butter and hydrogenated oils; absorbefacients such as quaternary ammonium bases and sodium lauryl sulfate; humectants such as glycerol and starch; adsorbents such as starch, lactose, kaolin, bentonite and colloidal silica; lubricants such as purified talc, stearic acid salts, boric acid powder and polyethylene glycol; and the like. The tablets may be provided as tablets coated with usual coatings, for example, sugar-coated tablets, gelatin-coated tablets, enteric coated tablets, film-coated tablets, double layer tablets, multilayer-coated tablets and the like.

Capsule preparations are formulated by mixing the compound according to the present invention with the various carriers exemplified above and charging the mixture into hard gelatin capsules, soft capsules and the like.

When the composition is prepared in the form of pills, there may be used, as carriers, excipients such as glucose, lactose, starch, cacao butter, hardened vegetable oils, kaolin and talc; binders such as gum arabic powder, tragacanth gum, gelatin and ethanol; disintegrators such as laminaran and agar; and the like.

Liquid preparations may be aqueous or oily suspensions, solutions, syrups or elixirs. These are prepared by using usual additives in accordance with a method known per se in the art.

The amount of the compound according to the present invention to be contained in the above preparations varies according to a preparation form, administration route, dosing plan and the like and hence cannot be absolutely said, and is suitably selected from a wide range. However, the compound may preferable be contained in a proportion of about 1–70 wt. % of the preparation.

No particular limitation is imposed on the administration method of the preparation, and an administration method such as enteral administration, oral administration, rectal administration, intraoral administration or percutaneous administration is suitably determined according to a preparation form, the age, sex and other conditions of a target to be dosed such as a patient, the diseased condition of the patient, and the like. For example, the tablets, pills, solutions, suspensions, emulsions, granules and capsules are orally dosed, while the suppositories are intrarectally dosed. The injections are intravenously dosed by themselves or in combination with a usual fluid replacement containing glucose, amino acids and/or the like, and further intraarterially, intramuscularly, intracutaneously or subcutaneously dosed by themselves as needed. The ointments are applied to the skin, oral mucosa membrane, etc.

The dose of the compound according to the present invention is suitably selected according to an administration method, the age, sex, diseased condition and kind of a tumor of a target to be dosed such as a patient, the kind of the compound to be dosed, and other conditions. In general, it is however desirable to dose the compound in a proportion of about 1–1,000 mg for the oral preparation, about 0.1–500 mg for the injection or about 5–1,000 mg for the suppository, per preparation to be dosed. Besides, a dose per day of the medicine in the form of any of the above dose forms is preferably set on the basis of an amount ranging generally from about 0.1 to 200 mg/kg of weight/day, preferably from about 0.5 to 100 mg/kg of weight/day. These preparations according to the present invention may be dosed at once or in about 2–4 installments a day.

No particular limitation is imposed on malignant tumors which can be remedied by administering the preparation containing the compound according to the present invention. Examples thereof include head and neck cancer, esophageal carcinoma, gastric cancer, colon cancer, rectum cancer, cancer of liver, gallbladder.bile duct cancer, pancreatic cancer, pulmonary carcinoma, breast cancer, ovarian cancer, bladder cancer, prostatic cancer, testicular tumor, osteochondrosarcoma, malignant lymphoma, leukemia, cervical cancer, skin carcinoma, brain tumor and the like.

EXAMPLES

The present invention will hereinafter be described in more detail by the following Referential Examples, Examples and Pharmacological Test Examples. However, it should be borne in mind that the present invention is not limited to and by these examples.

Referential Example 1

Synthesis of 5-O-tert-butyldimethylsilyl-1,2-O-isopropylidene-3-C-(2-trimethylsilylethynyl)-α-D-ribofuranose Dissolved in 60 ml of tetrahydrofuran were 6.3 ml (45 mmol) of trimethylsilylacetylene in an argon atmosphere, and the solution was stirred at −78° C. While keeping the temperature of the reaction solution at −70° C. or lower, n-butyllithium (n-hexane solution, 1.62 mol/liter; 27.8 ml, 45 mmol) was added dropwise over 30 minutes. Upon elapsed time of 30 minutes after the drop addition, 4.5 g (15 mmol) of 5-O-tert-butyldimethylsilyl-1,2-O-isopropylidene-α-D-erythropentofuranose-3-ulose dissolved in 30 ml of tetrahydrofuran were added dropwise over 10 minutes, and the mixture was stirred further for 3 hours. After 60 ml of a 1N aqueous; ammonium chloride solution were added to the reaction mixture, the temperature of the mixture was raised to room temperature. After the reaction mixture was extracted with ethyl acetate (3×35 ml), and the resultant organic layer was washed with a saturated aqueous solution (3×20 ml) of sodium chloride, the thus-washed organic layer was dried over sodium sulfate. After the organic layer was filtered, the solvent was distilled off, and the residue was purified by column chromatography on silica gel (eluted with 5% ethyl acetate-n-hexane), thereby obtaining 5.92 g (yield: 99%) of the title compound as a white powdered substance.

mp: 84°–86° C.

FAB-MS: m/z 401($MH^+$), 383($M^+$-OH).

$^1$H-NMR ($CDCl_3$) δ: 5.85(d,1H,H-1,$J_{1,2}$=3.8 Hz), 4.56(d, 1H,H-2,$J_{2,1}$=3.8 Hz), 4.01–3.94(m,3H,H-4,H-5), 3.05(s,1H, 3-OH,exchanged with $D_2O$), 1.56,1.37(s,each 3H,ipr), 0.91 (s,9H,tBu), 0.18(s,9H,Me), 0.06,0.03(s,each 3H,Me).

Elemental analysis: Calculated (as $C_{19}H_{36}O_5Si_2$): C, 56.96; H, 9.06. Found: C, 56.82; H, 9.25.

Referential Example 2

Synthesis of 5-O-benzoyl-3-C-ethynyl-1,2-O-isopropylidene-α-D-ribofuranose

Dissolved in 15 ml of tetrahydrofuran were 1.44 g (3.6 mmol) of the compound obtained in Referential Example 1, and 5.4 ml (5.4 mmol) of a 1N tetrabutylammonium fluoride in tetrahydrofuran solution were added, followed by stirring for 10 minutes at room temperature. The solvent was distilled off to obtain 5-O-tert-butyldimethylsilyl-3-C-ethynyl-1,2-O-isopropylidene-α-D-ribofuranose as a syrupy substance. This compound was dissolved in 30 ml of pyridine, and 0.92 ml (7.9 mmol) of benzoyl chloride was added under cooling with ice water, followed by stirring at room temperature for 2 hours. The solvent was distilled off under reduced pressure, and the residue was azeotropically distilled three times with toluene. The resultant residue was dissolved in 50 ml of ethyl acetate, and the solution was subjected to liquid separation by using 25 ml of water and a saturated aqueous solution of sodium hydrogencarbonate (3×25 ml) in that order, followed by drying of the resultant organic layer over sodium sulfate. After the thus-dried organic layer was filtered, the solvent was distilled off, and the residue was purified by column chromatography on silica gel (eluted with 0–5–10% ethyl acetate-n-hexane), thereby obtaining 1.07 g (yield: 93%) of the title compound as a yellow syrupy substance FAB-MS: m/z 319($MH^+$), 303($M^+$-Me).

$^1$H-NMR ($CDCl_3$) δ: 8.12–7.42(m,5H,benzoyl), 5.97(d, 1H,H-1,$J_{1,2}$=3.8 Hz), 4.76(d.d,1H,H-5a,$J_{5a,4}$=3.8 Hz,$J_{5a,5b}$= 12.0 Hz), 4.61(d.d,1H,H-5b,$J_{5b,4}$=7.4 Hz,$J_{5b,5a}$=12.0 Hz), 4.60(d,1H,H-2,$J_{2,1}$=3.8 Hz), 4.23(d.d,1H,H-4,$J_{4,5a}$=3.8 Hz,$J_{4,5b}$=7.4 Hz), 3.02(s,1H,3-OH,exchanged with $D_2O$), 2.63(s,1H,3-C≡CH), 1.62,1.41(s,each 3H,ipr).

Elemental analysis: Calculated (as $C_{17}H_{18}O_6$): C, 64.14; H, 5.70. Found: C, 64.08; H, 5.73.

Referential Example 3

Synthesis of methyl 2,3,5-tri-O-benzoyl-3-C-ethynyl-α,β-D-ribofuranose (1) Dissolved in 27 ml of absolute methanol were 637 mg (2.0 mmol) of the compound obtained in Referential Example 2, and 1.25 g (5.0 mmol) of pyridinium p-toluenesulfonate were added to heat the mixture under reflux for 3 days in an argon atmosphere. After cooling the reaction mixture to room temperature, the solvent was distilled off under reduced pressure, the residue was dissolved in 30 ml of ethyl acetate, and the solution was subjected to liquid separation by using 15 ml of water and a saturated aqueous solution of sodium hydrogencarbonate (3×15 ml) in that order, followed by drying of the resultant organic layer over sodium sulfate. After the thus-dried organic layer was filtered, the solvent was distilled off to obtain methyl 5-O-benzoyl-3-C-ethynyl-α,β-D-ribofuranose as a syrupy substance. This compound was azeotropically distilled three times with pyridine and then dissolved in 30 ml of pyridine. Under cooling with ice water, 2.32 ml (20 mmol) of benzoyl chloride and 367 mg (3 mmol) of dimethylaminopyridine were added to the solution to stir the mixture at 100° C. for 24 hours. After cooling the reaction mixture to room temperature, the solvent was distilled off under reduced pressure, and the residue was azeotropically distilled three times with toluene. The resultant residue was dissolved in 20 ml of ethyl acetate, and the solution was subjected to liquid separation by using 10 ml of water and a saturated aqueous solution of sodium hydrogencarbonate (3×10 ml) in that order, followed by drying of the resultant organic layer over sodium sulfate. After the thus-dried organic layer was filtered, the solvent was distilled off, and the residue was purified by column chromatography on silica gel (eluted with 0–10% ethyl acetate-n-hexane), thereby obtaining 825 mg (yield: 83%) of the title compound as a yellow syrupy substance.

EI-MS: m/z 500($M^+$).

$^1$H-NMR ($CDCl_3$) δ: 8.12–7.30(m,15H,benzoyl×3), 6.03 (d,0.66H,β-H-1,$J_{1,2}$=1.2 Hz), 5.82(d,0.33H,α-H-1,$J_{1,2}$=4.4 Hz), 5.47(d,0.33H,α-H-2,$J_{2,1}$=4.4 Hz), 5.17(d,0.66H,β-H-2, $J_{2,1}$=1.2 Hz), 51014 4.78(m,3H,α,β-H-4,H-5), 3.53(s,1.98, β-OMe), 3.45(s,0.99H,α-OMe), 2.86(s,0.66H,β-3-C≡CH), 2.78(s,0.38H,α-3-C≡CH).

Anomer ratio of α:β=1:2 (as determined by $^1$H-NMR).

Elemental analysis: Calculated (as $C_{29}H_{24}O_8$): C, 69.59; H, 4.83. Found: C, 69.32; H, 4.76.

2) Under cooling with ice water, 0.15 ml (2 mmol) of acetyl chloride was added to 5.0 ml of absolute methanol, and the mixture was stirred at room temperature for 20 minutes. To this solution, 637 mg (2.0 mmol) of the compound obtained in Referential Example 2 dissolved in 2.0 ml of absolute methanol were added dropwise, followed by stirring at room temperature for 2 days. The reaction mixture was neutralized with 1.5 ml of triethylamine, and the solvent was distilled off under reduced pressure. The residue was azeotropically distilled three times with pyridine and then dissolved in 30 ml of pyridine. Under cooling with ice water, 2.32 ml (20 mmol) of benzoyl chloride and 367 mg (3 mmol) of dimethylaminopyridine were added to the solution to stir the mixture at 100° C. for 24 hours. After cooling the reaction mixture to room temperature, the solvent was distilled off under reduced pressure, and the residue was azeotropically distilled three times with toluene. The resultant residue was dissolved in 20 ml of ethyl acetate, and the solution was subjected to liquid separation by using 10 ml of water and a saturated aqueous solution of sodium hydrogencarbonate (3×10 ml) in that order, followed by drying of the resultant organic layer over sodium sulfate. After the thus-dried organic layer was filtered, the solvent was distilled off, and the residue was purified by column chromatography on silica gel (eluted with 0–10% ethyl acetate-n-hexane), thereby obtaining 718 mg (yield: 72%) of the title compound as a yellow syrupy substance. The physical property values thereof were identical with those in the process (1) except that the number of protons in NMR was different.

Another ratio of α:β=1:1 (as determined by $^1$H-NMR).

(3) Under cooling with ice water, 1.94 ml (27.3 mmol) of acetyl chloride were added to 3.2 ml of water and 8.86 ml of methanol, and the mixture was stirred at room temperature for 20 minutes. To this solution, 318 mg (1 mmol) of the compound obtained in Referential Example 2 dissolved in 2.0 ml of methanol were added dropwise, followed by stirring at room temperature for 6 hours. The reaction mixture was neutralized with 4.5 ml of triethylamine, and the solvent was distilled off under reduced pressure to obtain methyl 5-O-benzoyl-3-C-ethynyl-α,β-D-ribofuranose as a syrupy substance. This compound was azeotropically distilled three times with pyridine and then dissolved in 30 ml of pyridine. Under cooling with ice water, 1.16 ml (10 mmol) of benzoyl chloride and 184 mg (1.5 mmol) of dimethylaminopyridine were added to the solution to stir the mixture at 100° C. for 24 hours. After cooling the reaction mixture to room temperature, the solvent was distilled off under reduced pressure. The residue was azeotropically distilled three times with toluene. The resultant residue was dissolved in 10 ml of ethyl acetate, and the solution was subjected to liquid separation by using 5 ml of water and a saturated aqueous solution of sodium hydrogencarbonate (3×5 ml) in that order, followed by drying of the resultant organic layer over sodium sulfate. After the thus-dried organic layer was filtered, the solvent was distilled off, and the residue was purified by column chromatography on silica gel (eluted with 0–10% ethyl acetate-n-hexane), thereby obtaining 435 mg (yield: 87%) of the title compound as a yellow syrupy substance. The physical property values thereof were identical with those in the process (1).

Anomer ratio of α:β=1:2 (as determined by $^1$H-NMR).

Referential Example 4

Synthesis of 1-O-acetyl-2,3,5-tri-O-benzoyl-3-C-ethynyl-α,β-D-ribofuranose

Dissolved in 1.75 ml of acetic acid and 0.22 ml of acetic anhydride were 264 mg (0.53 mmol) of the compound obtained in Referential Example 3 (3). Under cooling with ice water, 0.11 ml of concentrated sulfuric acid was added, and the mixture was stirred at room temperature for 4 hours. To the reaction mixture, 4 ml of chloroform were added, and the resultant mixture was subjected to liquid separation by using 0.4 ml of water, a saturated aqueous solution of sodium hydrogencarbonate (3×1.2 ml) and water (2×0.4 ml) in that order, followed by drying of the resultant organic layer over sodium sulfate. After the thus-dried organic layer was filtered, the solvent was distilled off, and the residue was purified by column chromatography on silica gel (eluted with chloroform), thereby obtaining 259 mg (yield: 93%) of the title compound as a syrupy substance.

EI-MS: m/z 528($M^+$). 485($M^+$-Ac).

$^1$N-NMR ($CDCl_3$) δ: 8.17–7.32(m,15H,benzoyl×3), 6.77 (d,0.33H,α-H-1,$J_{1,2}$=4.6 Hz), 6.39(d,0.66H,β-H-1,$J_{1,2}$=1.5 Hz), 6.19(d,0.66H,β-H-2,$J_{2,1}$=1.5 Hz), 6.07(d,0.33H,α-H-2, $J_{2,1}$=4.6 Hz), 5.07–4.79(m,3H,α,β-4,H-5), 2.89(s,0.66H, β-3-C≡CH), 2.18(s,0.33H,α-3-C≡CH), 2.14(s,1.98H,β-acetyl), 2.00(s,0.99H,α-acetyl).

Anomer ratio of α:β=1:2 (as determined by $^1$H-NMR).

Elemental analysis: Calculated (as $C_{30}H_{24}O_9$): C, 68.18; H, 4.58. Found: C, 68.01; H, 4.64.

Referential Example 5

Synthesis of 5-O-tert-butyldimethylsilyl-1,2O-isopropylidene-3-C-(1-propynyl)-α-D-ribofuranose Propyne gas was liquefied at −30° C. in an argon atmosphere to store about 0.5 ml of liquid propyne in a three-necked flask, to which 5 ml of tetrahydrofuran were added, and the mixture was stirred at −78° C. While keeping the temperature of the reaction mixture at −70° C. or lower, n-butyllithium (n-hexane solution, 1.63 mol/liter; 1.84 ml, 3.0 mmol) was added dropwise over 30 minutes. Upon elapsed time of 30 minutes after the drop addition, 302 mg (1.0 mmol) of 5-O-tert-butyldimethylsilyl-1,2-O-isopropylidene-α-D-erythro-pentofuranose-3-ulose dissolved in 2.5 ml of tetrahydrofuran were added dropwise over 10 minutes, and the mixture was stirred further for 2 hours. After 5 ml of a 1N aqueous ammonium chloride solution were added to the reaction mixture, the temperature of the mixture was raised to room temperature. After the reaction mixture was extracted with ethyl acetate (3×5 ml), and the resultant organic layer was washed with a saturated aqueous solution (3×3 ml) of sodium chloride, the thus-washed organic layer was dried over sodium sulfate. After the organic layer was filtered, the solvent was distilled off, and the residue was purified by column chromatography on silica gel (eluted with 5% ethyl acetate-n-hexane), thereby obtaining 320 mg (yield: 93%) of the title compound as a syrupy substance.

FAB-MS: m/z 327($M^+$-Me).

IR (neat): 2255 $cm^{-1}$ (—C≡C—).

$^1$H-NMR ($CDCl_3$) δ: 5.83(d,1H,H-1,$J_{1,2}$=3.6 Hz), 4.51(d, 1H,H-2,$J_{2,1}$=3.6 Hz), 4.00–3.91(m,3H,H-4,H-5), 2.97(s,1H, 3-OH,exchanged with $D_2O$), 1.87(s,3H,3-C≡C—$\underline{CH_3}$), 1.56,1.36(s,each 3H,ipr), 0.91(s,9H,tBu), 0.10,0.09(s,each 3H,Me).

Elemental analysis: Calculated (as $C_{17}H_{30}O_5Si$): C, 59.61; H, 8.83. Found: C, 59.38; H, 8.94.

Referential Example 6

Synthesis of 5-O-benzoyl-3-C-(1-propynyl)-1,2-O-isopropylidene-α-D-ribofuranose

Dissolved in 30-ml of tetrahydrofuran were 3.42 g (10.0 mmol) of the compound obtained in Referential Example 5, and 10.0 ml (10.0 mmol) of a 1N tetrabutylammonium fluoride in tetrahydrofuran solution were added, followed by stirring at room temperature for 20 minutes. The solvent was distilled off to obtain 3-C-(1-propynyl)-1,2-O-isopropylidene-α-D-ribofuranose as a syrupy substance. This compound was dissolved in 50 ml of pyridine, and 2.90 ml (25.0 mmol) of benzoyl chloride were added to the solution under cooling with ice water, followed by stirring at room temperature for 4 hours. The solvent was distilled off under reduced pressure, and the residue was azeotropically distilled three times with toluene. The resultant residue was dissolved in 100 ml of ethyl acetate, and the solution was subjected to liquid separation by using 50 ml of water and a saturated aqueous solution of sodium hydrogencarbonate (3×50 ml) in that order, followed by drying of the resultant organic layer over sodium sulfate. After the thus-dried organic layer was filtered, the solvent was distilled off, and the residue was purified by column chromatography on silica gel (eluted with 5–10–15% ethyl acetate-n-hexane), thereby obtaining 2.47 g (yield: 74%) of the title compound as a white powdered substance.

mp: 120°–122° C.

FAB-MS: m/z 333($MH^+$).

$^1$H-NMR ($CDCl_3$) δ: 8.09–7.43(m,5H,benzoyl), 5.92(d, 1H,H-1,$J_{1,2}$=3.6 Hz), 4.72(d.d,1H,H-5a,$J_{5a,4}$=3.4 Hz,$J_{5a,5b}$=11.9 Hz), 4.56(d,d,1H,H-5b,$J_{5b,4}$=7.7 Hz,$J_{5b,5a}$=11.9 Hz), 4.53(d,1H,H-2,$J_{2,1}$=3.6 Hz), 4.17(d,d,1H,H-4, $J_{4,5a}$=3.4 Hz,$J_{4,5b}$=7.7 Hz), 2.90 (s,1H,3-OH,exchanged with $D_2O$), 1.89(s,3H,3-C≡C—$\underline{CH_3}$), 160,139(s,each 3H,ipr).

Elemental analysis: Calculated (as $C_{18}H_{20}O_6$): C, 65.05; H, 6.07. Found: C, 64.92; H, 6.19.

Referential Example 7

Synthesis of methyl 2,3,4,5-tri-O-benzoyl-3-C-(1-propynyl)-α,β-D-ribofuranose

Under cooling with ice water, 13.4 ml (179 mmol) of acetyl chloride were added to 22.1 ml of water and 7.49 ml of methanol, and the mixture was stirred at room temperature for 20 minutes. To this solution, 2.3 g (6.9 mmol) of the compound obtained in Referential Example 6 were then added, followed by stirring at room temperature for 8 hours. The reaction mixture was neutralized with 30 ml of triethylamine, and the solvent was distilled off under reduced pressure to obtain methyl 5-O-benzoyl-3-C-(1-propynyl)-α,β-D-ribofuranose as a syrupy substance. This compound was azeotropically distilled three times with pyridine and then dissolved in 110 ml of pyridine. Under cooling with ice water, 8.0 ml (69 mmol) of benzoyl chloride and 1.27 g (10.4 mmol) of dimethylaminopyridine were added to the solution to stir the resultant mixture at 100° C. for 24 hours. After cooling the reaction mixture to room temperature, the solvent was distilled off under reduced pressure. The residue was azeotropically distilled three times with toluene. The resultant residue was dissolved in 150 ml of ethyl acetate, and the solution was subjected to liquid separation by using 50 ml of water and a saturated aqueous solution of sodium hydrogencarbonate (3×50 ml) in that order, followed by drying of the resultant organic layer over sodium sulfate. After the thus-dried organic layer was filtered, the solvent was distilled off, and the residue was purified by column chromatography on silica gel (eluted with 0–10% ethyl acetate-n-hexane), thereby obtaining 2.8 g (yield: 80%) of the title compound as a yellow syrupy substance.

FAB-MS: m/z 515($MH^+$), 483($M^+$-OMe).

$^1$H-NMR ($CDCl_3$) δ: 8.16–7.29(m,15H,benzoyl×3), 5.95 (s,0.6H,β-H-1), 5.79(d,0.4H,α-H-1,$J_{1,2}$=4.4 Hz), 5.45(d, 0.4H,α-H-2,$J_{2,1}$=4.4 Hz), 5.13(s,0.6H,β-H-2), 5.03–4.72(m, 3H,α,β-H-4,H-5), 3.51(s,1.8H,β-OMe), 3.43(s,1,2H,α-OMe), 1.90(s,1.8H,β-3-C≡C—$\underline{CH_3}$), 1.87(s,1.2H,α-3-C≡C—$\underline{CH_3}$)

Anomer ratio of α:β=2:3 (as determined by $^1$H-NMR).

Elemental analysis: Calculated (as $C_{30}H_{26}O_8$): C, 70.03; H, 5.09. Found: C, 69.77; H, 4.86.

Referential Example 8

Sythesis of 1-O-acetyl-2,3,5-tri-O-benzoyl-3-C(1-propynyl)-α,β-D-ribofuranose

Dissolved in 16.55 ml of acetic acid and 2.08 ml of acetic anhydride were 2.57 g (5.0 mmol) of the compound obtained in Referential Example 7. Under cooling with ice water, 1.04 ml of concentrated sulfuric acid were added, and the mixture was stirred at room temperature for 30 minutes. To the reaction mixture, 50 ml of chloroform were added, and the resultant mixture was subjected to liquid separation by using 5 ml of water, a saturated aqueous solution of sodium hydrogencarbonate (3×15 ml) and water (2×5 ml) in that order, followed by drying of the resultant organic layer over sodium sulfate. After the thus-dried organic layer was filtered, the solvent was distilled off, and the residue was purified by column chromatography on silica gel (eluted with 10–20% ethyl acetate-n-hexane), thereby obtaining 2.64 g (yield: 98%) of the title compound as a syrupy substance.

FAB-MS: m/z 543($MH^+$).

$^1$H-NMR ($CDCl_3$) δ: 8.16–7.34(m,15H,benzoyl×3), 6.75 (d,0.4H,α-H-1,$J_{1,2}$=4.4 Hz), 6.35(d,0.6H,β-H-1,$J_{1,2}$=1.5 Hz), 6.11(d,0.6H,β-H-2,$J_{2,1}$=1.5 Hz), 6.02(d,0.4H, α-H-2,$J_{2,1}$=4.4 Hz), 4.97–4.79(m,3H,α,β-H-4,H-5), 2.13(s, 1.8H,β-acetyl), 1.97(s,1.2H,α-acetyl), 1.92(s,1.8H,β-3-C≡C—$\underline{CH_3}$), 1.86(s,1.2H,α-3-C≡C—$\underline{CH_3}$).

Anomer ratio of α:β=2:3 (as determined by $^1$H-NMR).

Elemental analysis: Calculated (as $C_{31}H_{26}O_9$): C, 68.63; H, 4.83. Found: C, 68.45; H, 4.71.

Referential Example 9

Synthesis of 5-O-tert-butyldimethylsilyl-1,2-O-isopropylidene-3-C-(1-butynyl)-α-D-ribofuranose Butyne gas was liquefied at −30° C. in an argon atmosphere to store about 0.4 ml of liquid butyne in a three-necked flask, to which 5 ml of tetrahydrofuran were added, and the mixture was stirred at −78° C. While keeping the temperature of the reaction mixture at −70° C. or lower, n-butyllithium (n-hexane solution, 1.63 mol/liter; 1.84 ml, 3.0 mmol) was added dropwise over 30 minutes. Upon elapsed time of 30 minutes after the drop addition, 302 mg (1.0 mmol) of 5-O-tert-butyldimethylsilyl-1,2-O-isopropylidene-α-D-erythro-pentofuranose-3-ulose dissolved in 2.5 ml of tetrahydrofuran were added dropwise over 10 minutes, and the mixture was stirred further for 2 hours. After 5 ml of 1N aqueous ammonium chloride solution were added to the reaction mixture, the temperature of the mixture was raised to room temperature. After the reaction mixture was extracted with ethyl acetate (3×5 ml), and the resultant organic layer was washed with a saturated aqueous solution (3×3 ml) of sodium chloride, the thus-washed organic layer was dried over sodium sulfate. After the organic layer was filtered, the solvent was distilled off, and the residue was purified by column chromatography on silica gel (eluted with 5% ethyl acetate-n-hexane), thereby obtaining 259 mg (yield: 73%) of the title compound as a syrupy substance.

FAB-MS: m/z 341($M^+$-Me).

IR (neat): 2245 $cm^{-1}$ (—C≡C—).

$^1$H-NMR ($CDCl_3$) δ: 5.83(d,1H,H-1,$J_{1,2}$=3.5 Hz), 4.51(d, 1H,H-2,$J_{1,2}$=3.5 Hz), 4.06–3.92(m,3H,H-4,H-5), 2.97(s,1,3-OH,exchanged with $D_2O$), 2.24(m,2H,3-C≡C—$\underline{CH_2}CH_3$), 160,137(s,each 3H,ipr), 1.15(t,3H,J=7.4 Hz,3-C≡C—$CH_2\underline{CH_3}$), 0.91(s,9H,tBu), 0.11,0.09(s,each 3H,Me).

Elemental analysis: Calculated (as $C_{18}H_{32}O_5Si$): C, 60.64; H, 9.05. Found: C, 60.21; H, 9.12.

Referential Example 10

Synthesis of 5-O-benzoyl-3-C-(1-butynyl)-1,2O-isopropylidene-α-D-ribofuranose Dissolved in 30 ml of tetrahydrofuran were 3.56 g (10.0 mmol) of the compound obtained in Referential Example 9, and 10.0 ml (10.0 mmol) of a 1N tetrabutylammonium fluoride in tetrahydrofuran solution were added, followed by stirring for 20 minutes at room temperature. The solvent was distilled off to obtain 3-C-(1-butynyl)-1,2O-isopropylidene-α-D-ribofuranose as a syrupy substance. This compound was dissolved in 50 ml of pyridine, and 2.55 ml (22.0 mmol) of benzoyl chloride were added to the solution under cooling with ice water, followed by stirring at room temperature for 4 hours. The solvent was distilled off under reduced pressure, and the residue was azeotropically distilled three times with toluene. The resultant residue was dissolved in 100 ml of ethyl acetate, and the solution was subjected to liquid separation by using 50 ml of water and a saturated aqueous solution of sodium hydrogencarbonate (3×50 ml) in that order, followed by drying of the resultant organic layer over sodium sulfate. After the thus-dried organic layer was filtered, the solvent was distilled off, and the residue was purified by column chromatography on silica gel (eluted with 5–10–20% ethyl acetate-n-hexane), thereby obtaining 2.98 g (yield: 86%) of the title compound as a white powdered substance.

mp: 110°–113° C.

FAB-MS: m/z 347($MH^+$).

$^1$H-NMR ($CDCl_3$) δ: 8.09–7.42(m,5H,benzoyl), 5.93(d, 1H,H-1,$J_{1,2}$=3.6 Hz), 4.73(dd,1H,H-5a,$J_{5a,4}$=3.4 Hz,$J_{5a,5b}$=12.0 Hz), 4.56(d.d,1H,H-5b,$J_{5b,4}$=7.7 Hz,$J_{5b,5a}$=12.0 Hz), 4.53(d,1H,H-2,$J_{2,1}$=3.6 Hz), 4.18(d.d,1H,H-4,$J_{4,5a}$=3.4 Hz,$J_{4,5}$=7.7 Hz), 2.90(s,1H,3-OH,exchanged with $D_2O$), 2.26(m,2H,3-C≡C—$\underline{CH_2}CH_3$), 1.60,1.39(s,each 3H,ipr), 1.16(t,3H,J≡7.5 Hz,3-C≡C—$CH_2\underline{CH_3}$).

Elemental analysis: Calculated (as $C_{19}H_{22}O_6$): C, 65.88; H, 6.40. Found: C, 65.69; H, 6.52.

Referential Example 11

Synthesis of methyl 2,3,5-tri-O-benzoyl-3-C-(1-butynyl)-α,β-D-ribofuranose

Under cooling with ice water, 12.3 ml (164 mmol) of acetyl chloride were added to 20.3 ml of water and 69.0 ml of methanol, and the mixture was stirred at room temperature for 20 minutes. To this solution, 2.2 g (6.4 mmol) of the compound obtained in Referential Example 10 were then added, followed by stirring at room temperature for 10 hours. The reaction mixture was neutralized with 30 ml of triethylamine, and the solvent was distilled off under reduced pressure to obtain methyl 5-O-benzoyl-3-C-(1-butynyl)-α,β-D-ribofuranose as a syrupy substance. This compound was azeotropically distilled three times with pyridine and then dissolved in 100 ml of pyridine. Under cooling with ice water, 7.4 ml (64 mmol) of benzoyl chloride and 1.2 g (9.5 mmol) of dimethylaminopyridine were added to the solution to stir the resultant mixture at 100° C. for 24 hours. After cooling the reaction mixture to room temperature, the solvent was distilled off under reduced pressure. The residue was azeotropically distilled three times with toluene. The resultant residue was dissolved in 150 ml of ethyl acetate, and the solution was subjected to liquid separation by using 50 ml of water and a saturated aqueous solution of sodium hydrogencarbonate (3×50 ml) in that order, followed by drying of the resultant organic layer over sodium sulfate. After the thus-dried organic layer was filtered, the solvent was distilled off, and the residue was purified by column chromatography on silica gel (eluted with 0–10% ethyl acetate-n-hexane), thereby obtaining 3.0 g (yield: 88%) of the title compound as a yellow syrupy substance.

FAB-MS: m/z 529($MH^+$), 497($M^+$-OMe).

$^1$H-NMR ($CDCl_3$) δ: 8.16–7.31(m,15H,benzoyl×3), 5.96 (d,0.6H,β-1,$J_{1,2}$=0.9 Hz), 5.80(d,0.4H,α-H-1,$J_{1,2}$=4.4 Hz), 5.45(d,0.4H,α-H-2,$J_{2,1}$=4.4 Hz), 5.14(d,0.6H,β-H-2,$J_{2,1}$=0.9 Hz), 5.01–4.73(m,3H,α,β-H-4,H-5), 3.51(s,1.8H,β-OMe), 3.43(s,1,2H,α-OMe), 2.28–2.21(m,2H,α,β-3-C≡C—$\underline{CH_2}CH_3$). 1.14–1.10(m,3H,α,β-3-C≡C—$CH_2\underline{CH_3}$).

Anomer ratio of α:β=2:3 (as determined by $^1$H-NMR).

Elemental analysis: Calculated (as $C_{31}H_{28}O_8$): C, 70.44; H, 5.34. Found: C, 70.05; H, 5.11.

Referential Example 12

Synthesis of 1-O-acetyl-2,3,5-tri-O-benzoyl-3-C-(1-butynyl)-α,β-D-ribofuranose Dissolved in 16.89 ml of acetic acid and 2.13 ml of acetic anhydride were 2.69 g (5.1 mmol) of the compound obtained in Referential Example 11. Under cooling with ice water, 1.06 ml of concentrated sulfuric acid were added to the solution, and the mixture was stirred at room temperature for 30 minutes. To the reaction mixture, 50 ml of chloroform were added, and the resultant mixture was subjected to liquid separation by using 5 ml of water, a saturated aqueous solution of sodium hydrogencarbonate (3×15 ml) and water (2×5 ml) in that order, followed by drying of the resultant organic layer over sodium sulfate After the thus-dried organic layer was filtered, the solvent was distilled off, and the residue was purified by column chromatography on silica gel (eluted with 10% ethyl acetate-n-hexane), thereby obtaining 2.37 g (yield: 83%) of the title compound as a syrupy substance.

FAB-MS: m/z 557($MH^+$), 513($M^+$-Ac), 497($M^+$-OAc).

$^1$H-NMR ($CDCl_3$) δ: 8.16–7.34(m,15H,benzoyl×3), 6.75 (d,0.4H,α-H-1,$J_{1,2}$=4.5 Hz), 6.36(d,0.6H,β-H-1,$J_{1,2}$=1.1 Hz), 6.12(d,0.6H,β-H-2,$J_{2,1}$=1.1 Hz), 6.03(d,0.4H, α-H-2,$J_{2,1}$=4.5 Hz), 5.02–4.77(m,3H,α,β-H-4,H-5), 2.31–2.28(m, 1.2H,β-3-C≡C—$\underline{CH_2}CH_3$), 2.25–2.19(m, 0.8H,α-3-C≡C—$\underline{CH_2}CH_3$), 2.14(s,1.8H,β-acetyl), 1.99(s, 1.2H,α-acetyl), 1.18–1.15(m,1.8H,β-3-C≡C—$CH_2\underline{CH_e}$), 1.10–1.07(m,1.2H,α-3-C≡C—$CH_2\underline{CH_3}$).

Anomer ratio of α:β=2:3 (as determined by $^1$H-NMR).

Elemental analysis: Calculated (as $C_{32}H_{28}O_9$): C, 69.06; H, 5.07. Found: C, 68.88; H, 5.15.

Referential Example 13

Synthesis of 5-O-tert-butyldimethylsilyl-1,2-O-isopropylidene-3-C-ethenyl-α-D-ribofuranose Vinylmagnesium bromide (1N tetrahydrofuran solution, 30.0 ml, 30.0 mmol) was dissolved in 30 ml of tetrahydrofuran in an argon atmosphere, and the solution was stirred at −15° C. While keeping the temperature of the reaction solution at −10° C. or lower, 3.02 g (10.0 mmol) of 5-O-tert-butyldimethylsilyl-1,2-O-isopropylidene-α-D-erythro-pentofuranose-3-ulose dissolved in 40 ml of tetrahydrofuran were added dropwise over 30 minutes, and the mixture was stirred further for 2 hours. After 50 ml of a 1N aqueous ammonium chloride solution were added to the reaction mixture, the temperature of the mixture was raised to room temperature. After the reaction mixture was extracted with ethyl acetate (3×35 ml), and the resultant organic layer was washed with a saturated aqueous solution (3×30 ml) of sodium chloride, the thus-washed organic layer was dried over sodium sulfate. After the organic layer was filtered, the solvent was distilled off, and the residue was purified by column chromatography on silica gel (eluted with 5% ethyl acetate-n-hexane), thereby obtaining 2.11 g (yield: 64%) of the title compound as a syrupy substance.

FAB-MS: m/z 315($M^+$-Me).

$^1$H-NMR ($CDCl_3$) δ: 5.83(d,1H,H-1,$J_{1,2}$=3.8 Hz), 5.77 (d.d,1H,3-$\underline{CHc}$=CHaCHb,$J_{c,a}$=17.2 Hz,$J_{c,b}$=11.0 Hz), 5.53 (d.d,1H,3-CHc=$\underline{CHa}$CHb,$J_{a,c}$=17.2 Hz,$J_{a,b}$=1.5 Hz), 5.28 (d.d,1H,3-CHc=CHa$\underline{CHb}$,$J_{b,c}$=11.0 Hz,$J_{b,a}$=1.5 Hz), 4.22 (d, 1H,H-2,$J_{2,1}$=3.8 Hz), 3.98(t,1H,H-4,J=5.6 Hz), 3.69–3.67 (m,2H,H-5), 2.76(s,1H,3-OH,eschanged with $D_2O$), 1.61, 1.35(s,each 3H,ipr), 0.88(s,9H,tBu), 0.06,0.05 (s,each 3H,Me).

Referential Example 14

Synthesis of 5-O-benzoyl-3-C-ethenyl-1,2O-isopropylidene-α-D-ribofuranose

Dissolved in 20 ml of tetrahydrofuran were 1.67 g (5.1 mmol) of the compound obtained in Referential Example 13, and 5.1 ml (5.1 mmol) of a 1N tetrabutylammonium fluoride in tetrahydrofuran solution were added, followed by stirring for 20 minutes at room temperature. The solvent was distilled off to obtain 5-O-tert-butyldimethylsilyl-3-C-ethenyl-1,2-O-isopropylidene-α-D-ribofuranose as a syrupy substance. This compound was dissolved in 35 ml of pyridine, and 1.72 ml (15.0 mmol) of benzoyl chloride were added to the solution under cooling with ice water, followed by stirring at room temperature for 4 hours. The solvent was distilled off under reduced pressure, and the residue was azeotropically distilled three times with toluene. The resultant residue was dissolved in 65 ml of ethyl acetate, and the solution was subjected to liquid separation by using 25 ml of water and a saturated aqueous solution of sodium hydrogencarbonate (3×25 ml) in that order, followed by drying of the resultant organic layer over sodium sulfate. After the thus-dried organic layer was filtered, the solvent was distilled off, and the residue was purified by column chromatography on silica gel (eluted with 5–10–20% ethyl acetate-n-hexane), thereby obtaining 1.46 g (yield: 90%) of the title compound as a white powdered substance.

mp: 110°–111° C.

FAB-MS: m/z 321($MH^+$), 305($M^+$-Me).

$^1$H-NMR ($CDCl_3$) δ: 8.07–7.42(m,5H,benzoyl), 5.91(d, 1H,H-1,$J_{1,2}$=3.8 Hz) 5.81(d.d,1H,3-$\underline{CHc}$=CHaCHb,$J_{c,a}$=17.3 Hz,$J_{c,b}$=11.0 Hz), 5.60(d.d,1H,3-CHc=$\underline{CHa}$CHb,$J_{a,c}$=17.3 Hz,$J_{a,b}$=1.3 Hz), 5.36(d.d,1H,3-CHc=CHa$\underline{CHb}$,$J_{b,c}$=11.0 Hz, $J_{b,a}$=1.3 Hz), 4.45(d.d,1H,H-5a,$J_{5a,4}$=2.9 Hz,$J_{5a,b}$=12.1 Hz), 4.30(d.d,1H,H-5b,$J_{5b,4}$=8.1 Hz,$J_{5b,5a}$=12.1 Hz), 4.26(d,1H,H-2,$J_{2,1}$=3.8 Hz), 4.21(d.d, 1H,H-4,$J_{4,5a}$=2.9 Hz,$J_{4,5b}$=8.1 Hz), 2.84(s,1H,3-OH, exchanged with $D_2O$), 1.62,1.38(s,each 3H,ipr).

Elemental analysis: Calculated (as $C_{17}H_{20}O_6$): C, 63.74; H, 6.29. Found: C, 63.75; H, 6.21.

Referential Example 15

Synthesis of methyl 2,3,5-tri-o-benzoyl-3-C-ethenyl-α,β-D-ribofuranose

Under cooling with ice water, 10.3 ml (137 mmol) of acetyl chloride were added to 17.0 ml of water and 57.6 ml of methanol, and the mixture was stirred at room temperature for 20 minutes. To this solution, 1.7 g (5.3 mmol) of the compound obtained in Referential Example 14 were added, followed by stirring at room temperature for 5 hours. The reaction mixture was neutralized with 20 ml of triethylamine, and the solvent was distilled off under reduced pressure to obtain methyl 5-O-benzoyl-3-C-ethenyl-α,β-D-ribofuranose as a syrupy substance. This compound was azeotropically distilled three times with pyridine and then dissolved in 85 ml of pyridine. Under cooling with ice water, 6.2 ml (53 mmol) of benzoyl chloride and 0.97 g (8.0 mmol) of dimethylaminopyridine were added to the solution to stir the resultant mixture at 100° C. for 24 hours. After cooling the reaction mixture to room temperature, the solvent was distilled off under reduced pressure. The residue was azeotropically distilled three times with toluene. The resultant residue was dissolved in 120 ml of ethyl acetate, and the solution was subjected to liquid separation by using 35 ml of water and a saturated aqueous solution of sodium hydrogencarbonate (3×35 ml) in that order, followed by drying of the resultant organic layer over sodium sulfate. After the thus-dried organic layer was filtered, the solvent was distilled off, and the residue was purified by column chromatography on silica gel (eluted with 0–10% ethyl acetate-n-hexane), thereby obtaining 1.7 g (yield: 66%) of the title compound as a yellow syrupy substance.

FAB-MS: m/z 487($M^+$-Me), 471($M^+$-OMe).

$^1$H-NMR ($CDCl_3$) δ: 8.14–7.24(m,15H,benzoyl×3), 6.36 (d.d,0.75H,β-3-$\underline{CHc}$=CHaCHb,$J_{c,a}$=17.6 Hz,$J_{c,b}$=11.2 Hz), 6.22(d.d,0.25H,α-3-$\underline{CHc}$=CHaCHb,$J_{c,a}$=17.6 Hz,$J_{c,b}$=11.2 Hz), 5.86(s,0.75H,β-H-1), 5.72(d,0.25H,α-H-1,$J_{1,22}$=4.7 Hz), 5.45(d,0.25H,α-H-2,$J_{2,1}$=4.7 Hz), 5.40–5.33(m,2H,α, β-3-CHc=$\underline{CHaCHb}$), 5.15(s,0.75H,β-H-2), 4.95–4.93(m, 1H,α,β-H-4), 4.75(d.d,0.25H,α-H-5a,$J_{5a,4}$=3.9 Hz,$J_{5a,5b}$= 11.9 Hz), 4.69(d.d,0.75H,β-H-5a,$J_{5a,4}$=4.2 Hz,$J_{5a,5b}$=11.8 Hz), 4.57(d.d,0.75H,α-H-5b,$J_{5b,4}$=6.2 Hz,$J_{5b,5a}$=11.9 Hz), 4.51(d.d,0.75H,β-H-5b,$J_{5b,4}$=7.2 Hz,$J_{5b,5a}$'11.8 Hz), 3.53(s, 2.25H,β-OMe), 3.44(s,0.75H,α-OMe).

Anomer ratio of α:β=1:3 (as determined by $^1$H-NMR).

Elemental analysis: Calculated (as $C_{29}H_{26}O_8$): C, 69.31; H, 5.21. Found: C, 69.45; H, 5.00.

Referential Example 16

Synthesis of 1-O-acetyl-2,3,5-tri-O-benzoyl-3-C-ethenyl-α,β-D-ribofuranose

Dissolved in 9.86 ml of acetic acid and 1.24 ml of acetic anhydride were 1.50 g (2.98 mmol) of the compound obtained in Referential Example 15. Under cooling with ice water, 0.62 ml of concentrated sulfuric acid was added, and the mixture was stirred at room temperature for 30 minutes. To the reaction mixture, 23 ml of chloroform were added, and the resultant mixture was subjected to liquid separation by using 3 ml of water, a saturated aqueous solution of sodium hydrogencarbonate (3×7 ml) and water (2×3 ml) in that order, followed by drying of the resultant organic layer over sodium sulfate. After the thus-dried organic layer was filtered, the solvent was distilled off, and the residue was purified by column chromatography on silica gel (eluted with 10–20% ethyl acetate-n-hexane), thereby obtaining 1.27 g (yield: 80%) of the title compound as a yellow syrupy substance.

FAB-MS: m/z 531($MH^+$).

$^1$H-NMR ($CDCl_3$) δ: 8.15–7.31(m,15H,benzoyl×3), 6.73 (d,0.33H,α-H-1,$J_{1,2}$=4.7 Hz), 6.40(d,0.66H,β-H-1,$J_{1,2}$=1.3 Hz), 6.33(d.d,0.66H,β-3-CHc=CHaCHb,$J_{c,a}$=17.4 Hz,$J_{c,b}$=11.3 Hz), 6.26(d.d,0.33H,α-3-CHc=CHaCHb,$J_{c,a}$=17.5 Hz,$J_{c,b}$=11.4 Hz), 6.04(d,0.66H,β-H-2,$J_{2,1}$=1.3 Hz), 5.97(d, 0.33H,α-H-2,$J_{2,1}$=4.7 Hz), 5.48–5.41(m,2H,α,β-3-CHc=CHaCHb), 5.27–5.03(m,1H,α,β-H-4), 4.78–4.50(m,2H,α,β-H-5), 2.14(s,1.98H,β-acetyl), 1.97(s,0.99H,α-acetyl).

Anomer ratio of α:β=1:2 (as determined by $^1$H-NMR).

Elemental analysis: Calculated (as $C_{30}H_{26}O_9$): C, 67.92; H, 4.94. Found: C, 67.75; H, 4.83.

Example 1

Synthesis of 1-(2,3,5-tri-O-benzoyl-3-C-ethynyl-β-D-ribofuranosyl)cytosine (Compound 1)

Added to 222 mg (2.0 mmol) of cytosine were 2.0 ml of hexamethyldisilazane and 7 mg of ammonium sulfate in an argon atmosphere, and the mixture was heated under reflux until cytosine was completely dissolved. After the reaction mixture was cooled to room temperature, the solvent was distilled off under reduced pressure while keeping dry, and the residue was azeotropically distilled three times with toluene. To the resultant residue, 264 mg (0.5 mmol) of the compound obtained in Referential Example 4 dissolved in 4 ml of anhydrous acetonitrile were added, followed by addition of 0.29 ml (2.5 mmol) of tin tetrachloride at 0° C. The mixture was stirred at room temperature for 18 hours. The reaction mixture was added with 12 ml of chloroform and 5 ml of a saturated aqueous solution of sodium hydrogencarbonate, and stirred at room temperature for 30 minutes. The precipitate formed was then separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with 5% methanol-chloroform), thereby obtaining 235 mg (yield: 81%) of the title Compound 1 as a foamy substance.

FAB-MS: m/z 580($MH^+$).

$^1$H-NMR ($CDCl_3$) δ: 8.15–7.31(m,15H,benzoyl×3), 7.76 (d,1H,H-6,$J_{6,5}$=7.5 Hz), 6.60(d,1H,H-1',$J_{1',2'}$=5.2 Hz), 6.06 (d,1H,H-2',$J_{2',1'}$=5.2 Hz), 5.72(d,1H,H-5,$J_{5,6}$=7.5 Hz), 4.96–4.89(m,3H,H-4',H-5'), 2.88(s,1H,3'-C≡CH).

Example 2

Synthesis of 1-(3-C-ethynyl-β-D-ribofuranosyl) cytosine (Compound 2)

Dissolved in 9 ml of methanolic ammonia were 200 mg (0.35 mmol) of Compound 1 obtained in Example 1, and the solution was stirred at room temperature for 2 days. The solvent was distilled off under reduced pressure, and the residue was purified by column chromatography on silica gel (eluted with 5–20% methanol-chloroform), thereby obtaining 83.0 mg (yield: 90%) of the title Compound 2 as a white powdered substance.

mp: 233°–235° C.

EI-MS: m/z 267($M^+$), 250($M^+$-OH).

IR (nujor): 2115 $cm^{-1}$ (—C≡C—).

UV: $\lambda_{max}$ ($H_2O$) 270 nm (ε9,100);

$\lambda_{max}$ (0.5N hydrochloric acid) 280 nm (ε13,400);

$\lambda_{max}$ (0.5N sodium hydroxide) 272 nm (ε9, 300).

$^1$H-NMR (DMSO-$d_6$) δ: 7.86(d,1H,H-6,$J_{6,5}$=7.7 Hz), 7.25,7.18(bs,each 1H,—NH,exchanged with $D_2O$), 5.88(d, 1H,H-1',$J_{1',2'}$=6.6 Hz), 5.84(s,1H,3'-OH,exchanged with $D_2O$), 5.79(d,1H,2'-OH,$J_{2'\text{-}OH,2'}$=6.6 Hz,exchanged with $D_2O$), 5.78(d,1H,H-5,$J_{5,6}$=7.7 Hz), 5.06(d.d,1H,5=-OH,$J_{5'\text{-}OH,5'a}$=4.4 Hz,$J_{5'\text{-}OH,5'b}$=5.5 Hz, exchanged with $D_2O$), 4.16 (t,1H,H-2',J=6.6 Hz), 3.92–3.89(m,1H,H-4'), 3.74–3.71(m, 2H,H-5'), 3.55(s,1H,3'-C≡CH).

Elemental analysis: Calculated (as $C_{11}H_{13}N_3O_5$): C, 49.45; H, 4.90; N, 15.72. Found: C, 49.55; H, 4.76, N, 15.70.

Example 3

Synthesis of 1-(2,3,5-tri-O-benzoyl-3-C-ethynyl-β-D-ribofuranosyl)-5-fluorocytosine (Compound 3)

Added to 258 mg (2.0 mmol) of 5-fluorocytosine were 2.0 ml of hexamethyldisilazane and 7 mg of ammonium sulfate in an argon atmosphere, and the mixture was heated under reflux until 5-fluorocytosine was completely dissolved. After the reaction mixture was cooled to room temperature, the solvent was distilled off under reduced pressure while keeping dry, and the residue was azeotropically distilled three times with toluene. To the resultant residue, 264 mg (0.5 mmol) of the compound obtained in Referential Example 4 dissolved in 4 ml of anhydrous acetonitrile were added, followed by addition of 0.29 ml (2.5 mmol) of tin tetrachloride at 0° C. The mixture was stirred at room temperature for 18 hours. The reaction mixture was added with 12 ml of chloroform and 5 ml of a saturated aqueous solution of sodium hydrogencarbonate, and stirred at room temperature for 30 minutes. The precipitate formed was then separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with 5% methanol-chloroform), thereby obtaining 224 mg (yield: 81%) of the title Compound 3 as a foamy substance.

FAB-MS: m/z 598($MH^+$).

$^1$H-NMR ($CDCl_3$) δ: 8.15–7.31(m,15H,benzoyl×3), 7.77 (d,1H,H-6,$J_{6,5\text{-}F}$=6.1 Hz), 6.54(d,1H,H-1',$J_{1',2'}$=5.1 Hz), 6.03(d,1H,H-2',$J_{2',1'}$=5.1 Hz), 4.97–4.96(m,2H,H-5'), 4.91–4.89(m,1H,H-4'), 2.90(s,1H,3'-C≡CH).

Example 4

Synthesis of 1-(3-C-ethynyl-β-D-ribofuranosyl)-5-fluorocytosine (Compound 4)

Dissolved in 8 ml of methanolic ammonia were 189 mg (0.32 mmol) of Compound 3 obtained in Example 3, and the solution was stirred at room temperature for 2 days. The solvent was distilled off under reduced pressure, and the residue was purified by column chromatography on silica gel (eluted with 5–20% methanol-chloroform), thereby obtaining 81.0 mg (yield: 89%) of the title Compound 4 as a white powdered substance.

mp: 242° C. (decomposed).

EI-MS: m/z 285($M^+$).

IR (nujor): 2115 $cm^{-1}$ (—C≡C—).

$^1$H-NMR (DMSO-$d_6$) δ: 8.11(d,1H,H-6, $J_{6,5\text{-}F}$=7.2 Hz), 7.82,7.57(bs,each 1H,—NH,exchanged with $D_2O$), 5.84 (d.d,1H,H-1',$J_{1',2'}$=6.9 Hz,$J_{1',5\text{-}F}$=1.9 Hz), 5.8(s,1H,3'-OH, exchanged with $D_2O$), 5.72(d,1H,2'-OH,$J_{2'\text{-}OH,2'}$=6.6 Hz,exchanged with $D_2O$), 5.14(t,1H,5'-OH,J=4.5 Hz,exchanged with $D_2O$), 4.13(d.d,1H,H-2',$J_{2',1'}$= 6.9 Hz,$J_{2',2'\text{-}OH}$=6.6 Hz) 3.88–3.87(m,1H,H-4'), 3.75–3.60 (m,2H,H-5'), 3.53(s,1H,3'-C≡CH).

Elemental analysis: Calculated (as $C_{11}H_{12}FN_3O_5$): C, 46.32; H, 4.24; F, 6.66; N, 14.73. Found: C, 46.12; H, 4.28, F, 6.61; N, 14.69.

Example 5

Synthesis of 1-(2,3,5-tri-O-benzoyl-3-C-ethynyl-β-D-ribofuranosyl)uracil (Compound 5) and 3-(2,3,5-tri-O-benzoyl-3-C-ethynyl-β-D-ribofuranosyl)uracil (Compound 6)

Added to 225 mg (2.0 mmol) of uracil were 2.0 ml of hexamethyldisilazane and 7 mg of ammonium sulfate in an argon atmosphere, and the mixture was heated under reflux until uracil was completely dissolved. After the reaction mixture was cooled to room temperature, the solvent was distilled off under reduced pressure while keeping dry, and the residue was azeotropically distilled three times with toluene. To the resultant residue, 264 mg (0.5 mmol) of the compound obtained in Referential Example 4 dissolved in 4 ml of anhydrous acetonitrile were added, followed by addition of 0.23 ml (2.0 mmol) of tin tetrachloride at 0C. The mixture was stirred at room temperature for 2 days. The reaction mixture was added with 12 ml of chloroform and 5 ml of a saturated aqueous solution of sodium hydrogencarbonate, and stirred at room temperature for 30 minutes. The precipitate formed was then separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with 0–5% methanol-chloroform), thereby obtaining 167 mg of the title Compound 5 (eluted with chloroform, yield: 58%) and 57 mg of the title Compound (6 (eluted with 5%-methanol-chloroform, yield: 20%), both, as foamy substances. Compound 5:

FAB-MS: m/z 581($MH^+$).

$^1$H-NMR ($CDCl_3$) δ: 8.13–7.30(m,15H,benzoyl×3), 8.05 (br,1H,—NH,exchanged with $D_2O$), 7.71(d,1H,H-6,$J_{6,5}$=8.2 Hz), 6.38(d,1H,H-1',$J_{1',2'}$=5.0 Hz), 6.01(d,1H,H-2',$J_{2',1'}$=5.0 Hz), 5.74(d,d,1H,H-5,$J_{5,6}$=8.2 Hz,$J_{5,NH}$=2.0 Hz), 4.98–4.87 (m,3H,H-4',H-5'), 2.92(s,1H,3'-C≡CH).

Compound 6

FAB-MS: m/z 581($MH^+$).

$^1$H-NMR ($CDCl_3$) δ: 9.26(bs,1H,—NH,exchanged with $D_2O$), 8.14–7.29(m,16H,benzoyl×3,H-6), 6.92(d,1H,H-1', $J_{1',2'}$=6.8 Hz), 6.69(d,1H,H-2',$J_{2',1'}$=6.8 Hz), 5.82(d,1H,H-5, $J_{5,6}$=7.6 Hz), 5.04–4.88(m,3H,H-4',H-5'), 2.82(s,1H,3'-C≡CH).

Example 6

Another synthesis of 1-(2,3,5-tri-O-benzoyl-3-C-ethynyl-β-D-ribofuranosyl)uracil (Compound 5)

Added to 225 mg (2.0 mmol) of uracil were 2.0 ml of hexamethyldisilazane and 7 mg of ammonium sulfate in an argon atmosphere, and the mixture was heated under reflux until uracil was completely dissolved. After the reaction mixture was cooled to room temperature, the solvent was distilled off under reduced pressure while keeping dry, and the residue was azeotropically distilled three times with toluene. To the resultant residue, 264 mg (0.5 mmol) of the compound obtained in Referential Example 4 dissolved in 4 ml of anhydrous acetonitrile were added, followed by addition of 0.39 ml (2.0 mmol) of trimethylsilyl trifluoromethanesulfonate at 0° C. The mixture was stirred at room temperature for 5 hours. After the reaction mixture was added with 12 ml of chloroform and 5 ml of a saturated aqueous solution of sodium hydrogencarbonate, and stirred at room temperature for 30 minutes, the reaction mixture was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 274 mg (yield: 95%) of the title Compound 5 as a foamy substance.

Example 7

Synthesis of 1-(3-C-ethynyl-β-D-ribofuranosyl) uracil (Compound 7)

Dissolved in 10 ml of methanolic ammonia were 150 mg (0.26 mmol) of Compound 5 obtained in Example 5 or 6, and the solution was stirred at room temperature for 2 days. The solvent was distilled off under reduced pressure, and the residue was purified by column chromatography on silica gel (eluted with 5–15% methanol-chloroform), thereby obtaining 59.4 mg (yield: 85%) of the title Compound 7 as a white powdered substance.

mp: 226°–228° C.

EI-MS: m/z 268($M^+$).

IR (nujor): 2110 $cm^{-1}$ (—C≡C—).

UV: λmax ($H_2O$,0.5N hydrochloride acid) 261 nm (ϵ10, 200);

$\lambda_{max}$ (0.5N sodium hydroxide) 262 nm (ϵ7,500).

$^1$H-NMR (DMSO-$d_6$) δ: 11.35(bs,1H,—NH,exchanged with $D_2O$), 7.99(d,1H,H-6,$J_{6,5}$=8.2 Hz), 5.93(s,1H,3'-OH, exchanged with $D_2O$), 5.86(d,1H,2'-OH,$J_{2'\text{-}OH,2'}$6.7 Hz, exchanged with $D_2O$), 5.86(d,1H,2'-OH,$J_{2'\text{-}OH,2'}$=6.7 Hz, exchanged with $D_2O$), 5.83(d,1H,H-1',$J_{1',2'}$=7.3 Hz), 5.69(d, 1H,H-5,$J_{5,6}$=8.2 Hz), 5.13(t,1H,5'-OH,J=4.5 Hz,exchanged with $D_2O$), 4.18(d.d,1H,H-2',$J_{2',1'}$=7.3 Hz,$J_{2',2'\text{-}OH}$=6.7 Hz), 3.90–3.88(m,1H,H-4'), 3.74–3.60(m,2H,H-5'), 3.55(s,1H,3'-C≡CH).

Elemental analysis: Calculated (as $C_{11}H_{12}N_2O_6$): C, 49.26; H, 4.51; N, 10.44. Found: C, 49.00; H, 4.64, N, 10.52.

Example 8

Synthesis of 3-(3-C-ethynyl-β-D-ribofuranosyl) uracil (Compound 8)

Dissolved in 1.5 ml of methanolic ammonia were 55 mg (0.10 mmol) of Compound 6 obtained in Example 5, and the solution was stirred at room temperature for 2 days. The solvent was distilled off under reduced pressure, and the residue was purified by column chromatography on silica gel (eluted with 5–15% methanol-chloroform), thereby obtaining 17.1 mg (yield: 67%) of the title Compound 8 as a white powdered substance.

mp: 255° C. (decomposed).

EI-MS: m/z 250($M^+$-OH), 237($M^+$-$CH_2OH$).

IR (nujor): 2230 $cm^{-1}$ (—C≡C—).

UV: $\lambda_{max}$ ($H_2O$) 264 nm (ε7,000);

$\lambda_{max}$ (0.5N hydrochloric acid) 264 nm (ε7,200);

$\lambda_{max}$ (0.5N sodium hydroxide) 293 nm (ε9,900).

$^1$H-NMR (DMSO-$d_6$) δ: 11.20(bs,1H,—NH,exchanged with $D_2O$), 7.47(d,1H,H-6,$J_{6,5}$=7.6 Hz), 6.09(d,1H,H-1', $J_{1',2'}$=8.3 Hz), 5.67(s,1H,3'—OH,exchanged with $D_2O$), 5.62 (d, 1H,2'-OH,$J_{2'-OH,2'}$=7.0 Hz,exchanged with $D_2O$), 5.60(d, 1H, H-5,$J_{5,6}$=7.6 Hz), 5.06(d.d,1H,H-2',$J_{2',1'}$=8.3 Hz,$J_{2',2'-OH}$=7.0 Hz), 4.48–4.46(m,1H,5'-OH,exchanged with $D_2O$), 3.86–3.84(m,1H,H-4'), 3.68–3.61(m,2H,H-5'), 3.37(s,1H,3'-C≡CH).

Elemental analysis: Calculated (as $C_{11}H_{12}N_2O_6$.1/2$H_2O$): C, 47.66; H, 4.73; N, 10.10. Found: C, 47.99; H, 4.66, N, 10.19.

Example 9

Synthesis of 1-(2,3,5-tri-O-benzoyl-3-C-ethynyl-β-D-ribofuranosyl)-5-fluorouracil (Compound 9)

Added to 262 mg (2.0 mmol) of 5-fluorouracil were 2.0 ml of hexamethyldisilazane and 7 mg of ammonium sulfate in an argon atmosphere, and the mixture was heated under reflux until 5-fluorouracil was completely dissolved. After the reaction mixture was cooled to room temperature, the solvent was distilled off under reduced pressure while keeping dry, and the residue was azeotropically distilled three times with toulene. To the resultant residue, 264 mg (0.5 mmol) of the compound obtained in Referential Example 4 dissolved in 4 ml of anhydrous acetonitrile were added, followed by addition of 0.23 ml (2.0 mmol) of tin tetrachloride at 0° C. The mixture was stirred at room temperature for 6.5 hours. The reaction mixture was added with 12 ml of chloroform and 5 ml of a saturated aqueous solution of sodium hydrogencarbonate, and stirred at room temperature for 30 minutes. Thereafter, the precipitate formed was separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 283 mg (yield: 95%) of the title Compound 9 as a foamy substance.

FAB-MS: m/z 599($MH^+$).

$^1$H-NMR ($CDCl_3$) δ: 8.16(bs,1H,—NH,exchanged with $D_2O$), 8.14–7.30(m,15H,benzoyl×3),7.83(d,1H,H-6,$J_{6,5\text{-}F}$= 5.8 Hz), 6.35(d.d,1H,H-1',$J_{1',2'}$=4.9 Hz,$J_{1',5\text{-}F}$=1.7 Hz), 5.79 (d,1H,H-2',$J_{2',1'}$=4.9 Hz), 4.96–4.95(m,2H,H-5'), 4.89–4.87 (m,1H,H-4'), 2.95(s,1H,3'-C≡CH).

Example 10

Synthesis of 1-(3-C-ethynyl-β-D-ribofuranosyl)-5-fluorouracil (Compound 10)

Dissolved in 12 ml of methanolic ammonia were 276 mg (0.46 mmol) of Compound 9 obtained in Example 9, and the solution was stirred at room temperature for 2 days. The solvent was distilled off under reduced pressure, and the residue was purified by column chromatography on silica gel (eluted with 5–20% methanol-chloroform), thereby obtaining 121 mg (yield: 92%) of the title Compound 10 as a white powdered substance.

EI-MS: m/z 286($M^+$), 251($M^+$-OH).

$^1$H-NMR (DMSO-$d_6$) δ: 11.87(bs,1H,—NH,exchanged with $D_2O$), 8.33(d,1H,H-6,$J_{6,5\text{-}F}$=7.2 Hz), 5.93(s,1H,3'-OH, exchanged with $D_2O$), 5.83(d.d,1H,H-1',$J_{1',2'}$=7.2 Hz,$J_{1'5\text{-}F}$= 1.8 Hz), 5.82(d,1H,2'-OH,$J_{2'-OH,2'}$=6.4 Hz,exchanged with $D_2O$), 5.27(t,1H5'-OH,J=4.1 Hz,exchanged with $D_2O$), 4.18 (d.d,1H,H-2',$J_{2',1'}$=7.2 Hz,$J_{2',2'-OH}$=6.4 Hz), 3.92–3.91(m, 1H-4'), 3.77–3.64(m,2H,H-5'), 3.56(s,1H,3'-C≡CH).

Example 11

Synthesis of 1-(2,3,5-tri-O-benzoyl-3-C-ethynyl-β-D-ribofuranosyl)thymine (Compound 11)

Added to 252 mg (2.0 mmol) of thymine were 2.0 ml of hexamethyldisilazane and 7 mg of ammonium sulfate in an argon atmosphere, and the mixture was heated under reflux until thymine was completely dissolved. After the reaction mixture was cooled to room temperature, the solvent was distilled off under reduced pressure while keeping dry, and the residue was azeotropically distilled three times with toluene. To the resultant residue, 264 mg (0.5 mmol) of the compound obtained in Referential Example 4 dissolved in 4 ml of anhydrous acetonitrile were added, followed by addition of 0.23 ml (2.0 mmol) of tin tetrachloride at 0° C. The mixture was stirred at room temperature for 27 hours. The reaction mixture was added with 12 ml of chloroform and 5 ml of a saturated aqueous solution of sodium hydrogencarbonate, and stirred at room temperature for 30 minutes. Thereafter, the precipitate formed was separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 290 mg (yield: 98%) of the title Compound 11 as a foamy substances.

FAB-MS: m/z 595($MH^+$).

$^1$H-NMR ($CDCl_3$) δ: 8.17–7.34(m,17H,benzoyl×3,H-6, —NH), 6.44(d,1H,H-1',$J_{1',2'}$=5.9 Hz), 6.06(d,1H,H-2',$J_{2',1'}$= 5.9 Hz), 4.98–4.95(m,1H,H-4'), 4.93–4.90(m,2H,H-5'), 2.91 (s,1H,3'-C≡CH), 1.72(s,3H,5-Me).

Example 12

Synthesis of 1-(3-C-ethynyl-β-D-ribofuranosyl) thymine (Compound 12)

Dissolved in 12 ml of methanolic ammonia were 290 mg (0.49 mmol) of Compound 11 obtained in Example 11, and the solution was stirred at room temperature for 2 days. The solvent was distilled off under reduced pressure, and the residue was purified by column chromatography on silica gel (eluted with 5–20% methanol-chloroform), thereby obtaining 115 mg (yield: 83%) of the title Compound 12 as a white powdered substance.

mp: 113°–118° C.

EI-MS: m/z 282($M^+$).

IR (nujor): 2115 $cm^{-1}$ (—C≡C—).

UV: $\lambda_{max}$ ($H_2O$) 266 nm (ε8,800);

$\lambda_{max}$ (0.5N hydrochloric acid) 265 nm ($\epsilon$8,600);
$\lambda_{max}$ (0.5N sodium hydroxide) 267 nm ($\epsilon$7,000).

$^1$H-NMR (DMSO-$d_6$) δ: 11.30(bs,1H,—NH,exchanged with $D_2O$), 7.85(d,1H,H-6,$J_{6,5\text{-}Me}$=1.0 Hz), 5.90(s,1H,3'-OH,exchanged with $D_2O$), 5.83(d,1H,H-1',$J_{1',2'}$=7.5 Hz), 5.81(d,1H,2'-OH,$J_{2'\text{-}OH,2'}$=6.7 Hz,exchanged with $D_2O$), 5.13(t,1H,5'-OH,J=4.4 Hz,exchanged with $D_2O$), 4.19(d.d, 1H,H-2',$J_{2',1'}$=7.5 Hz,$J_{2',2'\text{-}OH}$=6.7 Hz), 3.88–3.86(m,1H,H-4'), 3.74–3.65(m,2H,H-5'), 3.55(s,1H,3'-C≡CH), 1.73(d, 3H,5-Me,$J_{5\text{-}Me,6}$=1.0 Hz).

Elemental analysis: Calculated (as $C_{12}H_{14}N_2O_6$.MeOH): C, 49.68; H, 5.77; N, 8.91. Found: C, 49.62; H, 5.81, N, 8.97.

Example 13

Synthesis of 9-(2,3,5-tri-O-benzoyl-3-C-ethynyl-β-D-ribofuranosyl)-N$^6$-benzoyladenine (Compound 13)

Added to 478 mg (2.0 mmol) of N$^6$-benzoyladenine were 6.0 ml of hexamethyldisilazane and 2 ml of pyridine in an argon atmosphere, and the mixture was heated under reflux until N$^6$-benzoyladenine was completely dissolved. After the reaction mixture was cooled to room temperature, the solvent was distilled off under reduced pressure while keeping dry, and the residue was azeotropically distilled three times with toluene. To the resultant residue, 264 mg (0.5 mmol) of the compound obtained in Referential Example 4 dissolved in 4 ml of anhydrous acetonitrile was added, followed by addition of 0.35 ml (3.0 mmol) of tin tetrachloride at 0° C. The mixture was stirred at room temperature for 7 hours. The reaction mixture was added with 12 ml of chloroform and 5 ml of a saturated aqueous solution of sodium hydrogencarbonate, and stirred at room temperature for 30 minutes. Thereafter, the precipitate formed was separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 261 mg (yield: 74%) of the title Compound 13 as a foamy substance.

FAB-MS: m/z 708(MH$^+$).

$^1$H-NMR ($CDCl_3$) δ: 8.99(bs,1H,—NHBz,exchanged with $D_2O$), 8.75(s,1H,H-8), 8.49(s,1H,H-2), 8.16–7.31(m, 15H,benzoyl×3), 6.58(d,1H,H-1',$J_{1',2'}$=4.8 Hz), 6.56(d,1H, H-2',$J_{2',1'}$=4.8 Hz), 5.07–5.03(m,2H,H-5'), 4.98–4.94(m,1H, H-4'), 2.95(s,1H,3'-C≡CH).

Example 14

Synthesis of 9-(3-C-ethynyl-β-D-ribofuranosyl) adenine (Compound 14)

Dissolved in 5 ml of methanolic ammonia were 234 mg (0.33 mmol) of Compound 13 obtained in Example 13, and the solution was stirred at room temperature for 2 days. The solvent was distilled off under reduced pressure, and the residue was purified by column chromatography on silica gel (eluted with 5–20% methanol-chloroform), thereby obtaining 80 mg (yield: 83%) of the title Compound 14 as a white powdered substance.

EI-MS: m/z 291(M$^+$), 274(M$^+$-OH).

$^1$H-NMR (DMSO-$d_6$) δ: 8.35(s,1H,H-8), 8.14(s,1H,H-2), 7.36(bs,2H,-$NH_2$, exchanged with $D_2O$), 5.99(s,1H,3'-OH, exchanged with $D_2O$), 5.88(d,1H2'-OH,$J_{2'\text{-}OH,2'}$=7.2 Hz,exchanged with $D_2O$), 5.85(d,1H,H-1',$J_{1',2'}$=7.8 Hz), 5.60(d.d,1H,5'-OH,$J_{5'\text{-}OH,5'a}$=7.4 Hz,$J_{5'\text{-}OH,5'b}$=4.0 Hz, exchanged with $D_2O$), 4.81(d.d,1H,H-2',$J_{2',1'}$=7.8 Hz,$J_{2',2'\text{-}OH}$=7.2 Hz), 4.01–3.08(m,1H,H-4'), 3.79–3.69(m,2H,H-5'), 3.54(s,1H,3'-C≡CH).

Example 15

Synthesis of 9-(2,3,5-tri-O-benzoyl-3-C-ethynyl-β-D-ribofuranosyl)-N$^2$-acetylguanine (Compound 15)

Added to 386 mg (2.0 mmol) of N$^2$-acetylguanine were 6.0 ml of hexamethyldisilazane and 2 ml of pyridine in an argon atmosphere, and the mixture was heated under reflux until N$^2$-acetylguanine was completely dissolved. After the reaction mixture was cooled to room temperature, the solvent was distilled off under reduced pressure while keeping dry, and the residue was azeotropically distilled three times with toluene. To the resultant residue, 264 mg (0.5 mmol) of the compound obtained in Referential Example 4 dissolved in 4 ml of anhydrous acetonitrile were added, followed by addition of 0.35 ml (3.0 mmol) of tin tetrachloride at 0° C. The mixture was stirred at room temperature for 2 hours. The reaction mixture was added with 12 ml of chloroform and 5 ml of a saturated aqueous solution of sodium hydrogencarbonate, and stirred at room temperature for 30 minutes. Thereafter, the precipitate formed was separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 327 ml (yield: 99%) of the title Compound 15 as a foamy substance.

FAB-MS: m/z 662(MH$^+$).

$^1$H-NMR $CDCl_3$) δ: 12.26(bs,1H,1-NH,exchanged with $D_2O$), 10.36(bs,1H,2-NHAc,exchanged with $D_2O$), 8.38(s, 1H,H-8), 8.15–7.28(m,15H-benzoyl×3), 6.85(d,1H, H-1',$J_{1',2'}$=3.9 Hz), 6.32(d,1H,H-2',$J_{2',1'}$=3.9 Hz), 5.09–5.05 (m,1H, H-4'), 5.04–4.86(m,2H,H-5'), 2.97(s,1H,3'-C≡CH), 2.36(s, 3H,2-NHAc).

Example 16

Synthesis of 9-(3-C-ethynyl-β-D-ribofuranosyl) guanine (Compound 16)

Suspended in 30 ml of methanol were 320 mg (0.49 mmol) of Compound 15 obtained in Example 15, and 0.90 ml (0.25 mmol) of sodium methoxide was added to the suspension. The resultant mixture was stirred at room temperature for 2 hours. After the reaction mixture was neutralized with Amberlite IRC-50s (a carboxylic resin), it was subjected to filtration by means of suction, and the filtrate was distilled under reduced pressure. The resultant residue was dissolved in 150 ml of water, and the solution was subjected to liquid separation using chloroform (2×100 ml). The water layer was distilled off under reduced pressure, thereby obtaining 95 mg (yield: 63%) of the title Compound 16 as a white powdered substance.

mp: 225° C. (decomposed).

EI-MS: m/z 307(M$^+$).

$^1$H-NMR (DMSO-$d_6$) δ: 10.95(bs,1H,1-NH), 8.28(s,1H, H-8), 6.25(bs,2H,—$NH_2$), 6.03(d,1H,H-1',$J_{1',2'}$=7.4 Hz), 5.92(s,1H,3'-OH), 5.86(d,1H,2'-OH,$J_{2'\text{-}OH,2'}$=6.5 Hz), 4.93 (t,1H,5'-OH,J=5.0 Hz), 4.62(d.d,1H,H-2',$J_{2',1'}$=7.4 Hz,$J_{2',2'\text{-}}$ $_{OH}$=6.5 Hz), 3.94–3.92(m,1H,H-4'), 3.75–3.66(m,2H,H-5'), 3.53(s,1H,3'-C≡CH).

Elemental analysis: Calculated (as $C_{12}H_{13}N_5O_5$): C, 46.90; H, 4.26; N, 22.80. Found: C, 46.80; H, 4.40, N, 22.85.

Example 17

Synthesis of 1-(2,3,5-tri-O-benzoyl-3-C-(1-propynyl)-β-D-ribofuranosyl)cytosine (Compound 17)

Added to 222 mg (2.0 mmol) of cytosine were 2.0 ml of hexamethyldisilazane and 7 mg of ammonium sulfate in an argon atmosphere, and the mixture was heated under reflux until cytosine was completely dissolved. After the reaction mixture was cooled to room temperature, the solvent was distilled off under reduced pressure while keeping dry, and the residue was azeotropically distilled three times with toluene. To the resultant residue, 271 mg (0.5 mmol) of the compound obtained in Referential Example 8 dissolved in 4 ml of anhydrous acetonitrile were added, followed by addition of 0.29 ml (2.5 mmol) of tin tetrachloride at 0° C. The mixture was stirred at room temperature for 2.5 hours. The reaction mixture was added with 12 ml of chloroform and 5 ml of a saturated aqueous solution of sodium hydrogencarbonate, and stirred at room temperature for 30 minutes. Thereafter, the precipitate formed was separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with 5% methanol-chloroform), thereby obtaining 214 mg (yield: 72%) of the title Compound 17 as a foamy substance.

FAB-MS: m/z 594($MH^+$).

$^1$H-NMR $CDCl_3$) δ: 8.15–7.31(m,15H,benzoyl×3), 7.82 (d,1H,H-6,$J_{6,5}$=7.5 Hz), 6.52(d,1H,H-1',$J_{1',2'}$=4.6 Hz), 6.03 (d,1H,H-2',$J_{2',1'}$=4.6 Hz), 5.74(d,1H,H-5,$J_{5,6}$=7.5 Hz), 4.96–4.86(m,3H,H-4',H-5'), 1.86(s,3H,3'-C≡C—$\underline{CH_3}$).

Example 18

Synthesis of 1-(3-C-(1-propynyl)-β-D-ribofuranosyl)cytosine (Compound 18)

Dissolved in 6 ml of methanolic ammonia were 150 mg (0.25 mmol) of Compound 17 obtained in Example 17, and the solution was stirred at room temperature for 2 days. The solvent was distilled off under reduced pressure, and the residue was purified by column chromatography on silica gel (eluted with 5–20% methanol-chloroform), thereby obtaining 63.0 mg (yield: 89%) of the title Compound 18 as a pale-yellow powdered substance.

mp: 162°–165° C.

EI-MS: m/z 281($M^+$).

$^1$H-NMR (DMSO-$d_6$+$D_2O$) δ: 8.26(d,1H,H-6,$J_{6,5}$=7.9 Hz), 6.15(d,1H,H-5,$J_{5,6}$=7.9 Hz), 5.78(d,1H,H-1',$J_{1',2'}$=5.7 Hz), 4.08(d,1H,H-2',$J_{2',1'}$=5.7 Hz), 3.95–3.94(m,1H,H-4'), 3.75(d.d,1H,H-5'a,$J_{5'a,4'}$=4.7 Hz,$J_{5'a,b}$=12.0 Hz), 3.67(d.d, 1H,H-5'b,$J_{5'b,4'}$=2.5 Hz,$J_{5'b,a}$=12.0 Hz), 1.81(s,3H,3'-C≡C—$\underline{CH_3}$).

Elemental analysis: Calculated (as $C_{12}H_{15}N_3O_5$.HCl.1/5$H_2O$): C, 44.85; H, 5.14; N, 13.08. Found: C, 44.72; H, 5.10, N, 12.93.

Example 19

Synthesis of 1-(2,3,5-tri-O-benzoyl-3-C-(1-butynyl)-β-D-ribofuranosyl)cytosine (Compound 19)

Added to 444 mg (4.0 mmol) of cytosine were 4.0 ml of hexamethyldisilazane and 14 mg of ammonium sulfate in an argon atmosphere, and the mixture was heated under reflux until cytosine was completely dissolved. After the reaction mixture was cooled to room temperature, the solvent was distilled off under reduced pressure while keeping dry, and the residue was azeotropically distilled three times with toluene. To the resultant residue, 556 mg (1.0 mmol) of the compound obtained in Referential Example 12 dissolved in 8 ml of anhydrous acetonitrile were added, followed by addition of 0.59 ml (5.0 mmol) of tin tetrachloride at 0° C. The mixture was stirred at room temperature for 19 hours. The reaction mixture was added with 25 ml of chloroform and 10 ml of a saturated aqueous solution of sodium hydrogencarbonate, and stirred at room temperature for 30 minutes. Thereafter, the precipitate formed was separated by filtration through Celite. The filtrate was subjected to liquid separation using water (2×10 ml) and 10 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with 5% methanol-chloroform), thereby obtaining 412 mg (yield: 68%) of the title Compound 19 as a foamy substance.

FAB-MS: m/z 608($MH^+$).

$^1$H-NMR ($CDCl_3$) δ: 8.15–7.31(m,15H,benzoyl×3), 7.84 (d,1H,H-6,$J_{6,5}$=7.4 Hz), 6.54(d,1H,H-1',$J_{1',2'}$=4.6 Hz), 6.04 (d,1H,H-2',$J_{2',1'}$=4.6 Hz), 5.72(d,1H,H-5,$J_{5,6}$=7.4 Hz), 4.97–4.85(m,3H,H-4',H-5'), 2.25–2.20(m,2H,3'-C≡C—$\underline{CH_2}CH_3$), 1.08(t,3H,J=7.5 Hz,3'-C≡C—$CH_2\underline{CH_3}$).

Example 20

Synthesis of 1-(3-C-(1-butynyl)-β-D-ribofuranosyl) cytosine (Compound 20)

Dissolved in 12 ml of methanolic ammonia were 336 mg (0.55 mmol) of Compound 19 obtained in Example 19, and the solution was stirred at room temperature for 2 days. The solvent was distilled off under reduced pressure, and the residue was purified by column chromatography on silica gel (eluted with 5–20% methanol-chloroform), thereby obtaining 154 mg (yield: 95%) of the title Compound 20 as a pale-yellow foamy substance.

mp: 181°–184° C.

EI-MS: m/z 295($M^+$).

$^1$H-NMR (DMSO-$d_6$+$D_2O$) δ: 8.27(d,$_1$H,H-6,$J_{6,5}$=7.8 Hz), 6.18(d,1H,H-5,$J_{5,6}$=7.8 Hz), 5.77(d,1H,H-1',$J_{1',2'}$=5.5 Hz), 4.08(d,1H,H-2',$J_{2',1'}$=5.5 Hz), 3.96–3.95(m,1H,H-4'), 3.77–3.67(m,2H,H-5'), 2.27–2.17(m,2H,3'-C≡C—$\underline{CH_2}CH_3$), 1.05(t,3H,J=7.5 Hz,3'-C≡C—$CH_2\underline{CH_3}$).

Elemental analysis: Calculated (as $C_{13}H_{17}N_3O_5$.HCl): C, 47.07; H, 5.47; N, 12.67. Found: C, 46.91; H, 5.61, N, 12.50.

Example 21

Synthesis of 1-(2,3,5-tri-O-benzoyl-3-C-ethenyl-β-D-ribofuranosyl)cytosine (Compound 21)

Added to 222 mg (2.0 mmol) of cytosine were 2.0 ml of hexamethyldisilazane and 7 mg of ammonium sulfate in an argon atmosphere, and the mixture was heated under reflux until cytosine was completely dissolved. After the reaction mixture was cooled to room temperature, the solvent was distilled off under reduced pressure while keeping dry, and the residue was azeotropically distilled three times with toluene. To the resultant residue, 265 mg (0.5 mmol) of the compound obtained in Referential Example 16 dissolved in 4 ml of anhydrous acetonitrile were added, followed by addition of 0.29 ml (2.5 mmol) of tin tetrachloride at 0° C. The mixture was stirred at room temperature for 18 hours. The reaction mixture was added with 12 ml of chloroform and 5 ml of a saturated aqueous solution of sodium hydrogencarbonate, and stirred at room temperature for 30 minutes. Thereafter, the precipitate formed was separated by filtration through Celite. The filtrate was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with 5% methanol-chloroform), thereby obtaining 201 mg (yield: 69%) of the title Compound 21 as a foamy substance.

FAB-MS: m/z 582($MH^+$).

$^1$H-NMR ($CDCl_3$) δ: 8.12–7.38(m,16H,benzoyl×3, H-6), 6.61(d,1H,H-1',$J_{1',2'}$=7.6 Hz), 6.35(d.d,1H,3'-CHc═CHaCHb,$J_{c,a}$=17.4 Hz,$J_{c,b}$=11.0 Hz), 6.03(d,1H,H-2',$J_{2',1'}$=7.6 Hz), 5.61(d,1H,H-5,$J_{5,6}$=6.9 Hz), 5.40–5.33(m, 2H, 3'-CHc═CHaCHb), 5.20–5.12(m,1H,H-4'), 4.84–4.65 (m, 2H,H-5').

Example 22

Synthesis of 1-(3-C-ethenyl-β-D-ribofuranosyl) cytosine (Compound 22)

Dissolved in 13 ml of methanolic ammonia were 323 mg (0.55 mmol) of Compound 21 obtained in Example 21, and the solution was stirred at room temperature for 2 days. The solvent was distilled off under reduced pressure, and the residue was purified by column chromatography on silica gel (eluted with 5–20% methanol-chloroform), thereby obtaining 156 mg (yield: 96%) of the title Compound 22 as a white powdered substance.

mp: 194°–197° C.

EI-MS: m/z 296($M^+$).

$^1$H-NMR (DMSO-$d_6$) δ: 7.93(d,1H,H-6,$J_{6,5}$=7.5 Hz), 7.20,7.17(bs,each 1H,NH), 6.05(d.d,1H,3'-CHc═CHaCHb,$J_{c,a}$=17.2 Hz,$J_{c,b}$=10.6 Hz), 5.93(d,1H,H-1', $J_{1',2'}$=7.9 Hz), 5.75(d,1H,H-5,$J_{5,6}$=7.5 Hz), 5.46(d.d,1H, 3'-CHc═CHaCHb,$J_{a,c}$=17.2 Hz,$J_{a,b}$=2.0 Hz), 5.31(d,1H,2'-OH, $J_{2'-OH,2'}$=6.7 Hz), 5.23(d.d,1H,3'-CHc═CHa CHb,$J_{b,c}$=10.6 Hz,$J_{b,a}$=2.0 Hz), 5.21(t,1H,5'-OH,J=4.5 Hz), 4.77(s,1H,3'-OH), 4.13(d.d,1H,H-2',$J_{2',1'}$=7.9 Hz,$J_{2',2'-OH}$= 6.7 Hz), 3.76–3.75(m,1H,H-4'), 3.55–3.39(m,2H,H-5').

Elemental analysis: Calculated (as $C_{11}H_{15}N_3O_5$): C, 49.07; H, 5.62; N, 15.61. Found: C, 49.17; H, 5.48; N, 15.59.

Example 23

Synthesis of 1-(2,3,5-tri-O-benzoyl-3-C-(1-propynyl)-β-D-ribofuranosyl)uracil (compound 23)

Added to 225 mg (2.0 mmol) of uracil were 2.0 ml of hexamethyldisilazane and 7 mg of ammonium sulfate in an argon atmosphere, and the mixture was heated under reflux until uracil was completely dissolved. After the reaction mixture was cooled to room temperature, the solvent was distilled off under reduced pressure while keeping dry, and the residue was azeotropically distilled three times with toluene. To the resultant residue, 271 mg (0.5 mmol) of the compound obtained in Referential Example 8 dissolved in 4 ml of anhydrous acetonitrile were added, followed by addition of 0.39 ml (2.0 mmol) of trimethylsilyl trifluoromethanesulfonate at 0° C. The mixture was stirred at room temperature for 8 hours. After the reaction mixture was added with 12 ml of chloroform and 5 ml of a saturated aqueous solution of sodium hydrogencarbonate, and stirred at room temperature for 30 minutes, the reaction mixture was; subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 241 mg (yield: 81%) of the title Compound 23 as a foamy substance.

FAB-MS: m/z 595($MH^+$).

$^1$H-NMR $CDCl_3$) δ: 8.14–7.30(m,15H,benzoyl×3), 7.97 (br,1H,—NH,exchanged with $D_2O$), 7.78(d,1H,H-6,$J_{6,5}$=8.0 Hz), 6.32(d,1H,H-1',$J_{1',2'}$=4.5 Hz), 5.96(d,1H,H-2',$J_{2',1'}$=4.5 Hz), 5.75(d.d,1H,H-5,$J_{5,6}$=8.0 Hz,$J_{5,NH}$=2.0 Hz), 4.93–4.84 (m,3H,H-4',H-5'), 1.91(s,3H,3'-C≡C—$CH_3$).

Example 24

Synthesis of 1-(3-C-(1-propynyl)-β-D-ribofuranosyl)uracil (Compound 24)

Dissolved in 10 ml of methanolic ammonia were 236 mg (0.40 mmol) of Compound 23 obtained in Example 23, and the solution was stirred at room temperature for 2 days. The solvent was distilled off under reduced pressure, and the residue was purified by column chromatography on silica gel (eluted with 0–5%) methanol-chloroform), thereby obtaining 8.66 mg (yield: 77%) of the title Compound 24 as a white powdered substance.

mp: 211°–213° C.

EI-MS: m/z 283($MH^+$).

IR (nujor): 2240 $cm^{-1}$ (—C≡C—).

$^1$H-NMR (DMSO-$d_6$) δ: 11.33(bs,1H,—NH,exchanged with $D_2O$), 7.97(d,1H,H-6,$J_{6,5}$=8.2 Hz), 5.80(d,1H,H-1',$J_{1',1'}$=6.9 Hz), 5.75(d,1H2'-OH,$J_{2'-OH,2'}$=6.5 Hz,exchanged with $D_2O$), 5.70(s,1H3'-OH,exchanged with $D_2O$), 5.68(d.d,1H, H-5,$J_{5,6}$=8.2 Hz,$J_{5,NH}$=2.0 Hz), 5.04(t, 1H,5'-OH,J=4.6 Hz,exchanged with $D_2O$), 4.10(d.d,1H,H-2',$J_{2',1'}$=6.9 Hz,$J_{2',2'-OH}$=6.5 Hz), 3.87–3.85(m,1H,H-4'), 3.73–3.62(m,2H,H-5'), 1.83(s,3H,3'-C≡C—$CH_3$).

Elemental analysis: Calculated (as $C_{12}H_{14}N_2O_6$.1/5$H_2O$): C, 50.42; H, 5.08; N, 9.80. Found: C, 50.51; H, 4.96, N, 9.78.

Example 25

Synthesis of 1-(2,3,5-tri-O-benzoyl-3-C-(1-butynyl)-β-D-ribofuranosyl)uracil (Compound 25)

Added to 225 mg (2.0 mmol) of uracil were 2.0 ml of hexamethyldisilazane and 7 mg of ammonium sulfate in an argon atmosphere, and the mixture was heated under reflux until uracil was completely dissolved. After the reaction mixture was cooled to room temperature, the solvent was distilled off under reduced pressure while keeping dry, and the residue was azeotropically distilled three times with toluene. To the resultant residue, 278 mg (0.5 mmol) of the compound obtained in Referential Example 12 dissolved in 4 ml of anhydrous acetonitrile were added, followed by addition of 0.39 ml (2.0 mmol) of trimethylsilyl trifluoromethanesulfonate at 0° C. The mixture was stirred at room temperature. After 2 days, 0.19 ml (1.0 mmol) of trimethylsilyl trifluoromethanesulfonate was added, and the mixture was stirred further for 5 hours at room temperature. After the reaction mixture was added with 12 ml of chloroform and 5 ml of a saturated aqueous solution of sodium hydrogencarbonate, and stirred at room temperature for 30 minutes, the reaction mixture was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 294 mg (yield: 97%) of the title Compound 25 as a foamy substance.

FAB-MS: m/z 609($MH^+$).

$^1$H-NMR ($CDCl_3$) δ: 8.15–7.29(m15H,benzoyl×3), 8.02 (br,1H,NH), 7.82(d,1H,H-6,$J_{6,5}$=8.2 Hz), 6.34(d,1H, H-1'-$J_{1',2'}$=4.4 Hz), 5.97(d,1H,H-2',$J_{2',1'}$=4.4 Hz), 5.75(d.d, 1H,H-5', $J_{5,6}$=8.2 Hz,$J_{5,NH}$=2.3 Hz), 4.93–4.84(m,3H,H-4', H-5'), 2.30–2.25(m,2H,3'-C≡C—$\underline{CH_2}CH_3$), 1.12(t,3H,J= 7.5 Hz,3'-C≡C—$CH_2\underline{CH_3}$).

Example 26

Synthesis of 1-(3-C-(1-butynyl)-β-D-ribofuranosyl) uracil (Compound 26)

Dissolved in 10 ml of methanolic ammonia were 286 mg (0.47 mmol) of Compound 25 obtained in Example 25, and the solution was stirred at room temperature for 2 days. The solvent was distilled off under reduced pressure, and the residue was purified by column chromatography on silica gel (eluted with 0–5%) methanol-chloroform), thereby obtaining 129 mg (yield: 93%) of the title Compound 26 as a white powdered substance.

mp: 139°–142° C.

EI-MS: m/z 297($MH^+$).

$^1$H-NMR (DMSO-$d_6$) δ: 11.31(bs,1H,NH), 7.96(d,1H,H-6,$J_{6,5}$=7.8 Hz), 5.79(d,1H,H-1',$J_{1',2'}$=6.7 Hz), 5.74(d,1H,2'-OH), 5.67(brs,1H,3'-OH), 5.66(d,1H,H-5,$J_{5,6}$=7.8 Hz), 4.99 (t,1H,5'-OH), 4.08(d.d,1H,H-2',$J_{2',1'}$=6.7 Hz,$J_{2',OH}$=6.4 Hz), 3.87–3.86(m,1H,H-4'), 3.74–3.64(m,2H,H-5'), 2.23–2.19 (m,2H,3'-C≡C—$\underline{CH_2}CH_3$), 1.07(t,3H,J=7.5 Hz,3'-C≡$CH_2$ $\underline{CH_3}$).

Elemental analysis: Calculated (as $C_{13}H_{16}N_2O_6.3/5H_2O$): C, 50.85; H, 5.65; N, 9.12. Found: C, 50.72; H, 5.47, N, 9.20.

Example 27

Synthesis of 1-(2,3,5-tri-O-benzoyl-3-C-ethenyl-β-D-ribofuranosyl)uracil (Compound 27)

Added to 225 mg (2.0 mmol) of uracil were 2.0 ml of hexamethyldisilazane and 7 mg of ammonium sulfate in an argon atmosphere, and the mixture was heated under reflux until uracil was completely dissolved. After the reaction mixture was cooled to room temperature, the solvent was distilled off under reduced pressure while keeping dry, and the residue was azeotropically distilled three times with toluene. To the resultant residue, 265 mg (0.5 mmol) of the compound obtained in Referential Example 16 dissolved in 4 ml of anhydrous acetonitrile were added, followed by addition of 0.39 ml (2.0 ml) of trimethylsilyl trifluoromethanesulfonate at 0° C. The mixture was stirred at room temperature 21 hours. After the reaction mixture was added with 12 ml of chloroform and 5 ml of a saturated aqueous solution of sodium hydrogencarbonate, and stirred at room temperature for 30 minutes, it was subjected to liquid separation using water (2×5 ml) and 5 ml of a saturated aqueous solution of sodium hydrogencarbonate in that order, followed by drying of the resultant organic layer over sodium sulfate. After the thus-dried organic layer was filtered, the solvent was distilled off under reduced pressure, and the residue was purified by column chromatography on silica gel (eluted with chloroform), thereby obtaining 284 mg (yield: 98%) of the title Compound 27 as a foamy substance.

FAB-MS: m/z 583($MH^+$).

$^1$H-NMR $CDCl_3$) δ: 8.17–7.44(m,16H,benzoyl×3, H-6), 8.05(bs,1H,—NH,exchanged with $D_2O$), 6.52(d,1H, H-1',$J_{1',2'}$=7.7 Hz), 6.41(d.d,1H,3'-$\underline{CHc}$=CHaCHb,$J_{c,a}$=17.4 Hz,$J_{c,b}$=11.1 Hz), 6.03(d,1H,H-2',$J_{2',1'}$=7.7 Hz), 5.54(d.d,1H,H-5,$J_{5,6}$=8.2 Hz,$J_{5,NH}$=2.2 Hz), 5.43–5.41(m,2H,3'-CHc=$\underline{CHaCHb}$), 5.25(d.d,1H,H-4',$J_{4',5'}$=3.2 Hz,$J_{4',5'}$=3.7 Hz), 4.83 (d.d,1H,H-5'a,$J_{5'a,4'}$=3.5 Hz,$J_{5'a,5'b}$=12.6 Hz), 4.7(d.d,1H, H-5'b,$J_{5'b,4'}$=3.7 Hz,$J_{5'b,5'a}$= 12.6 Hz).

Example 28

Synthesis of 1-(3-C-ethenyl-β-D-ribofuranosyl) uracil (Compound 28)

Dissolved in 13 ml of methanolic ammonia were 279 mg (0.48 mmol) of Compound 27 obtained in Example 27, and the solution was stirred at room temperature for 2 days. The solvent was distilled off under reduced pressure, and the residue was purified by column chromatography on silica gel (eluted with 5–10% methanol-chloroform), thereby obtaining 121 mg (yield: 93%) of the title Compound 28 as a pale-yellow powdered substance.

mp: 219°–222° C.

EI-MS: m/z 271($MH^+$).

$^1$H-NMR (DMSO-$d_6$) δ: 11.32(bs,1H,—NH,exchanged with $D_2O$), 8.08(d,1H,H-6,$J_{6,5}$=8.0 Hz), 6.05(d.d,1H,3'-$\underline{CHc}$=CHaCHb,$J_{c,a}$=17.2 Hz,$J_{c,b}$=10.7 Hz), 5.95(d,1H,H-1', $J_{1',2'}$=8.0 Hz), 5.70(d.d,1H,H-5,$J_{5,6}$=8.0 Hz,$J_{5,NH}$=2.1 Hz) 5.48(d.d,1H,3'-CHc=$\underline{CHa}$CHb,$J_{a,c}$=17.2 Hz,$J_{a,b}$=1.9 Hz), 5.46(d,1H,2'-OH,$J_{2'-OH,2}$=7.0 Hz,exchanged with $D_2O$), 5.26(d.d,1H,3'-CHc=CHa$\underline{CHb}$,$J_{b,c}$=10.7 Hz,$J_{b,a}$=1.9 Hz), 5.24(t,1H,5'-OH,J=4.2 Hz,exchanged with $D_2O$), 4.90(s,1H, 3'-OH,exchanged with $D_2O$), 4.11(d.d,1H,H-2',$J_{2',1'}$=8.0 Hz,$J_{2',2'-OH}$=7.0 Hz), 3.78–3.76(m,1H,H-4'), 3.57–3.41(m, 2H,H-5').

Elemental analysis: Calculated (as $C_{11}H_{14}N_2O_6$): C, 48.89; H, 5.22; N, 10.37. Found: C, 48.81; H, 5.18, N, 10.34.

Example 29

Synthesis of 1-(3-C-ethynyl-β-D-ribofuranosyl) cytosine 5'-monophosphate (Compound 29)

Dissolved in 14 ml of trimethyl phosphate were 267 mg (1.0 mmol) of Compound 2 obtained in Example 2, and 466 ml (5.0 mmol) of phosphorus oxychloride were added to the solution at −10° C., followed by stirring at 4° C. for 24 hours. After confirming the progress of the reaction by paper electrophoresis (0.05N triethylammonium bicarbonate buffer, 700 V, 1 hour), 100 ml of water and 100 ml of chloroform were added to the reaction mixture to conduct liquid separation. The resultant water layer was washed three times with chloroform. Water was added to the water layer to 400 ml, to which activated charcoal was added until the absorbance at 270 nm of the aqueous solution reached 0.5 or lower. The activated charcoal was mounted into a column (5 cm across×17 cm) and washed with 1,500 ml of water, followed by elution with 4,500 ml of ethanol. Fractions (each about 20 ml) of the aqueous solution, the absorbance at 270 nm of which was 0.5 or higher, were concentrated and dissolved in a small amount of ethanol. This solution was added to diethyl ether to form powder, and the powder was collected by filtration, thereby obtaining 299 mg (yield: 86%) of the title Compound 29 as a white powdered substance.

FAB-MS (negative): m/z 346($M^-$).

$^1$H-NMR ($D_2O$) δ: 8.25(d,1H,H-6,$J_{6,5}$=8.0 Hz), 6.32(d, 1H,H-5,$J_{5,6}$=8.0 Hz), 6.05(d,1H,H-1',$J_{1',2'}$,6.4 Hz), 4.47(d, 1H,H-2',$J_{2',1'}$=6.4 Hz), 4.39–4.37(m,1H,H-4'), 4.31–4.13 (m, 2H,H-5'), 3.13(s,1H,3'-C≡CH). $^{31}$P-NMR ($D_2O$, 85% $H_3PO_4$ (as internal standard)) δ: 0.24(s).

Example 30

Synthesis of 1-(3-C-ethynyl-β-D-ribofuranosyl) cytosine 5'-diphosphate (Compound 30) and 1-(3-C-ethynyl-β-D-ribofuranosyl)cytosine 5'-triphosphate (Compound 31)

Dissolved in 3 ml of anhydrous dimethylformamide were 36.8 mg (0.106 mmol) of Compound 29 obtained in Example 29 in an argon atmosphere, and 65.7 mg (0.405 mmol) of 1,1'-carbonyldiimidazole were added to the solution, followed by stirring at room temperature for 16 hours. After confirming the progress of the reaction by paper electrophoresis (0.05N triethylammonium bicarbonate buffer, 700 V, 1 hour), 27 ml (0.65 mmol) of methanol were added to the reaction mixture, followed by stirring at room temperature for 30 minutes. The resultant reaction mixture was added with 0.67 ml (0.67 mmol) of a 1M dimethylformamide solution of tributylammonium pyrophosphate and stirred at room temperature for 16 hours. After confirming the progress of the reaction by paper electrophoresis (0.05N triethylammonium bicarbonate buffer, 700 V, 1 hour), the precipitate formed was filtered off, and the filtrate was washed with 3 ml of dimethylformamide and 3 ml of ethanol and distilled under reduced pressure. After water was added to the residue to 100 ml of adsorb the residue on DEAE-Cellulofine A-200 (3 cm across×21 cm), and the residue was washed with 500 ml of water, elution was conducted with a 0–0.5N triethylammonium bicarbonate buffer (pH about 7.9, 1,700 ml) at a linear concentration gradient, thereby obtaining the title Compound 30 (eluted at 300 OD, 0.10–0.15N, yield: 31%) and Compound 31 (eluted at 80 OD, 0.18–0.22N, yield: 8%), both, as syrupy substances.

The purities of Compounds 30 and 31 were confirmed by a linear concentration gradient HPLC with 0.2–0.4M phosphate buffer (pH 7.0) using YNC-Pack IES-Ax.

Conditions:

Column: YMC-Pack IES-Ax.

Eluent: 0.2M (0.1 sec.)-0.4M (25 min.) phosphate buffer (pH 7.0).

Flow rate: 1.0 ml/min.

Detection wavelength: 254 nm.

Inject volume: 20 μl (0.5 mg/ml).

Temperature: room temperature.

Compound 30

Compound 31

Retention time: 9.8 min.

Retention time: 18.1 min.

Example 31

Synthesis of 1-(3-C-ethynyl-β-D-ribofuranosyl) uracil 5'-monophosphate (Compound 32)

After azeotropically distilling 100 mg of Compound 7 obtained in Example 7 three times with dioxane, it was dissolved in 10 ml of trimethyl phosphate, and 250 μl of phosphorus oxychloride were added to the solution at −0° C. in an argon atmosphere, followed by stirring at 4° C. for 24 hours. After confirming the progress of the reaction by paper electrophoresis (0.05N triethylammonium bicarbonate buffer (pH 8), 700 V, 45 minutes), 100 ml of a 0.2N triethylammonium bicarbonate buffer and 100 ml of chloroform were added to the reaction mixture to conduct liquid separation. The resultant water layer was washed twice with chloroform. The water layer was concentrated under reduced pressure, and the residue was dissolved in 500 ml of water to adsorb nucleic acid-derived substances in the aqueous solution on activated charcoal (the activated charcoal was added until the absorbance at 260 nm of the aqueous solution reached 0.2 or lower). The activated charcoal was mounted into a column (5 cm across×13 cm) and washed with 500 ml of water, followed by elution with 3,000 ml of ethanol. The resultant ethanol solution was concentrated under reduced pressure, and the residue was dissolved in 500 ml of water to apply the solution to a DEAE cellulose column. After washing with 500 ml of water, the residue was purified by using a 0–0.15N triethylammonium bicarbonate buffer at a linear concentration gradient, thereby obtaining the title Compound 32 (2,500 $OD_{260nm}$, yield: 62.5%).

FAB-MS: m/z 347(M—H).

$^1$H-NMR ($D_2O$) δ: 8.05(d,1H,J=8.2 Hz), 6.08(d,1H,J=6.9 Hz), 5.96(d,1H,J=8.2 Hz), 4.47(d,1H,J=6.9 Hz), 4.35(m, 1H), 4.28(m,1H), 4.16(m,1H), 3.15(s,1H).

$^{32}$P-NMR ($D_2O$, $H_3PO_4$ (as internal standard )) δ: 3.79(s).

Example 32

Synthesis of 1-(3-C-ethynyl-β-D-ribofuranosyl) uracil 5'-diphosphate (compound 33) and 1-(3-C-ethynyl-β-D-ribofuranosyl)uracil $5^1$-triphosphate (Compound 34)

After azeotropically distilling Compound 32 (550 $OD_{250nm}$, 0.055 mmol) obtained in Example 31 three times with dioxane , it was dissolved in 2 ml anhydrous dimethylformamide, and 30 mg of 1,1'-carbonyldiimidazole were added to the solution, followed by stirring at room temperature for 10 hours in an argon atmosphere. After confirming the progress of the reaction by paper electrophoresis (0.05N triethylammonium bicarbonate buffer (pH 8), 700 V, 45 minutes), 1 ml of dimethylformamide, in which 4.2 μl of methanol had been dissolved, was added to the reaction mixture, followed by stirring at room temperature for 30 minutes. The resultant reaction mixture was added with 300 μl of a 1M dimethylformamide solution of tributylammonium pyrophosphate and stirred at room temperature for 12 hours. After confirming the progress of the reaction by paper electrophoresis (0.05N triethylammonium bicarbonate buffer (pH 8), 700 V, 45 minutes), water was added to the reaction mixture to 500 ml in total, and the resultant mixture was applied to a DEAE cellulose column. After washing the mixture with 500 ml of water, elution was conducted with a 0–0.25N triethylammonium bicarbonate buffer at a linear concentration gradient, thereby obtaining the title Compound 33 (eluted at 230 $OD_{260nm}$, 0.15–0.16N, yield: 42%) and Compound 34 (eluted at 120 $OD_{260nm}$, 0.18–0.21N, yield: 22%).

Compounds 33 and 34 were confirmed with a 0.2–0.4M phosphate buffer (pH 7.0) using a ion-exchange HPLC (YMC-Pack IES-Ax) at a flow rate of 1.0 ml/min. As a result, their retention time were 8 minutes and 16 minutes. respectively.

Compound 33

FAB-MS: m/z 427(M—H).

$^1$H-NMR ($D_2O$) δ: 8.06(d,1H,J=8.0 Hz), 6.06(d,1H,J=6.9 Hz), 6.00(d,1H,J=8.0 Hz), 4.50(d,1H,J=6.9 Hz), 4.35(m, 1H), 4.32(m,1H), 4.28(m,1H), 3.15(s,1H).

$^{32}$P-NMR ($D_2O$, $H_3PO_4$ (as internal standard)) δ: −9.7 (m).

Compound 34

FAB-MS: m/z 507(M—H).

$^1$H-NMR ($D_2O$) δ: 8.06(d,1H,J=8.0 Hz), 6.08(d,1H,J=6.1 Hz), 6.00(d,1H,J=8.0 Hz), 4.50(d,1H,J=6.1 Hz), 4.35(m, 2H), 4.31(m,1H), 3.15(s,1H).

$^{32}$P-NMR ($D_2O$, $H_3PO_4$ (as internal standard)) δ: −9.58 (m), −9.76(m), −11.12(d).

Example 33

Synthesis of 1-(3-C-trimethylsilylethynyl-β-D-ribofuranosyl)uracil (Compound 35)

After a mixture of 30 ml of trifluoracetic acid and 3.0 ml of water was cooled to 0° C., 4.70 g of 1-(2,5-bis-O-(tert-butyldimethylsilyl)-f-D-erythro-pentofuran-3-ulosyl)uracil were added. After stirring at 0° C. for 20 minutes, the mixture was concentrated to dryness. After the residue was purified by medium-pressure preparative column chromatography ($SiO_2$, eluted with n-hexane:ethyl acetate=1.3), a mixture of n-hexane-ethyl acetate (10:1) was added to crystallize the product, thereby obtaining 2.40 g (yield: 67.3%) of 1-(2-O-tert-butyldimethylsilyl)-β-D-erythro-pentofuran-3-ulosyl)uracil.

After 2.24 g of cerium chloride heptahydrate were then heated at 140° C. for 5 hours under a reduced pressure of 0.2–0.3 Torr, it was cooled to room temperature, and its pressure was returned to ordinary pressure with nitrogen. After the thus-treated cerium chloride was cooled with ice water, 7 ml of tetrahydrofuran as distilled were added thereto, and the mixture was stirred overnight at room temperature. The thus-obtained suspension was cooled to −78° C.

On the other hand, 0.85 ml of trimethylsilylacetylene was added to 4 ml of tetrahydrofuran in a nitrogen atmosphere, and the mixture was cooled to −78° C. and then added with 3.61 ml of 1.66M n-butylithium/n-hexane. This mixture was stirred at −78° C. for 30 minutes, and then added dropwise to the cerium chloride suspension cooled to −78° C. by means of a syringe. After the resultant mixture was stirred at −78° C. for 1 hour, a solution of 356 mg of 1-(2-O-(tert-butyldimethylsilyl)-β-D-erythro-pentofuran-3-ulosyl)uracil obtained above in 2 ml of tetrahydrofuran was added thereto, followed by stirring for 2.5 hours. After 0.9 ml of acetic acid was added, the mixture was heated to room temperature, added with ethyl acetate and washed twice with saline. The ethyl acetate layer was dried over magnesium sulfate and then concentrated to dryness. To the residue, 4 ml of a mixture of ethyl acetate-n-hexane was added to crystallize it, thereby obtaining 358 mg (yield: 69.6%) of 1-(2-O-(tert-butyldimethylsilyl)-3-C-trimethylsilylethynyl-β-D-ribofuranosyl)uracil crystals as a monoacetate.

mp: 188°–189° C.

FAB-MS: m/z 455($MH^+$).

$^1$H-NMR (DMSO-$d_6$) δ: 11.96(br,1H,exchanged with $D_2O$), 11.39(d,1H,J=2.2 Hz,exchanged with $D_2O$), 8.06(d, 1H,J=8.1 Hz), 5.89(d,1H,J=7.2 Hz), 5.83(s,1H,exchanged with $D_2O$), 5.72(d.d,1H,J=8.1 Hz,2.2 Hz), 5.12(t,1H,J=3.9 Hz,exchanged with $D_2O$), 4.35(d,1H,J=7.2 Hz), 3.95(t,1H, J=3.2 Hz), 3.64–3.77(m,2H), 1.91(s,3H), 0.82(s,9H), 0.15 (s,9H), 0.09(s,3H), −0.04(s,3H).

Added to 2 ml of methanol were 309 mg of 1-(2-O-(tert-butyldimethylsilyl)-3-C-trimethylsilylethynyl-β-D-ribofuranosyl)uracil obtained above, and further 6 ml of 2.5% hydrochloric acid-methanol. After stirring the mixture at room temperature for 64 hours, it was concentrated under reduced pressure to dryness. To the residue, ethyl acetate was added to crystallize it, thereby obtaining 163 mg (yield: 80%) of the title Compound 35.

mp: 175°–177° C.

FAB-MS: m/z 341($MH^+$).

$^1$H-NMR (DMSO-$d_6$) δ: 11.36(br,1H, exchanged with $D_2O$), 7.94(d,1H,J=8.2 Hz), 5.92(s,1H,exchanged with $D_2O$), 5.85(d,1H,J=6.6 Hz,exchanged with $D_2O$), 5.79(d, 1H,J=6.6 Hz), 5.66(d,1H,J=8.2 Hz), 5.02(t,1H,J=4.5 Hz,exchanged with $D_2O$), 4.13(t,1H,J=6.6 Hz), 3.88(t,1H, J=3.7 Hz), 3.63–3.73(m,2H), 0.16(s,9H).

Example 34

Synthesis of 1-(3-C-triethylsilylethynyl-β-D-ribofuranosyl)uracil (Compound 36)

After 9.9 g of cerium chloride heptahydrate were dried at 140° C. for 40 hours under reduced pressure, its pressure was returned to ordinary pressure while introducing argon gas. While cooling with ice water and stirring vigorously, 31 ml of tetrahydrofuran were added at once to the cerium chloride, and the mixture was stirred overnight at room temperature.

After 4.77 ml of triethylsilylacetylene were added to 18 ml of tetrahydrofuran, and the mixture was cooled to −78° C. in an argon atmosphere, 15.8 ml of a 1.68M n-butyllithium/n-hexane solution were added dropwise over 20 minutes. After the drop addition, the mixture was stirred further for 30 minutes and added dropwise over about 10 minutes to the cerium chloride suspension cooled to −78° C. by means of a cannula. After completion of the drop addition, the mixture was stirred further for 60 minutes. A solution of 1.58 g of 1-(2-O-(tert-butyldimethylsilyl)-β-D-erythro-pentofuran-3-ulosyl)uracil in 9 ml of tetrahydrofuran was added dropwise over about 5 minutes to the mixture by means of the cannula. After 75 minutes, 4.8 ml of acetic acid were added to the reaction mixture, and the resultant mixture was then heated to room temperature. The mixture was subjected to liquid separation using 220 ml of ethyl acetate and 180 ml of water. After the resultant organic layer was washed with 180 ml of water and 100 ml saturated saline, it was dried over anhydrous sodium sulfate. After the drying, the solvent was distilled off under reduced pressure, and the residue was purified by column chromatography on silica gel (hexane:ethyl acetate=3:2), thereby obtaining 1.85 g (yield: 83%) of 1-(2-O-(tert-butyldimethylsilyl)-3-C-triethylsilylethynyl-β-D-ribofuranosyl)uracil as a white foamy substance.

EI-MS: m/z 496($M^+$), 481($M^+$−Me), 439($M^+$−tBu).

$^1$H-NMR (DMSO-$d_6$) δ: 11.30(brs,1H), 7.97(d,1H,J=8.1 Hz), 5.80(d,1H,J=7.3 Hz), 5.72(s,1H), 5.64(dd,1H,J=8.1 Hz), 5.02(t,1H), 4.27(d,1H,J=7.3 Hz), 3.88(t,1H), 3.63(m, 2H), 0.89(t,9H), 0.72(s,9H), 0.50(q,6H), −0.08(s,3H), −0.12 (s,3H).

Added to 1.8 g of 1-(2-O-(tert-butyldimethylsilyl)-3-C-triethylsilylethynyl-β-D-ribofuranosyl)uracil obtained above were 50 ml of a 2.6% (w/v) hydrochloric acid/methanol solution, and the mixture was stirred at room temperature. After 80 minutes, the solvent was distilled off under reduced pressure, and the residue was azeotropically distilled twice with ethanol and purified by column chromatography on covered silica gel (chloroform:methanol 50:1–15:1), thereby obtaining 1.3 g (yield: 91%) of the title compound as a white powdered substance.

mp: 194°–196° C.

EI-MS: m/z 382($M^+$), 353($M^+$−Et).

$^1$H-NMR (DMSO-$d_6$) δ: 9.35(brs,1H), 7.91(d,1H,J=8.2 Hz), 5.92(s,1H), 5.87(d,1H), 5.78(d,1H), 5.66(d,1HJ=8.2 Hz), 5.00(t,1H), 4.12(t,1H), 3.88(t,1H), 3.70(m,2H), 0.96(t, 9H), 0.57(q,6H).

Example 35

Synthesis of 1-(3-C-triisopropylsilylethynyl-β-D-ribofuranosyl)uracil (Compound 37)

After 22.4 g of cerium chloride heptahydrate were dried at 140° C. for 7 hours under reduced pressure, its pressure was returned to ordinary pressure while introducing argon gas. While cooling with ice water and stirring vigrously, 70 ml of tetrahydrofuran were added at once to the cerium chloride, and the mixture was stirred for 4 days at room temperature.

After 6.2 ml of triisopropylsilylacetylene were added to 18 ml of tetrahydrofuran, and the mixture was cooled to −78° C. in an argon atmosphere, 16.3 ml of a 1.68M n-butyllithium/n-hexane solution were added dropwise over 20 minutes. As a result, the solution was solidified, and so the solid was heated to −70° C. and stirred further for 30 minutes. The resultant solution was added dropwise over about 5 minutes to the cerium chloride suspension cooled to −78° C. by means of a syringe. After completion of the drop addition, the mixture was stirred further for 60 minutes. A solution of 1.63 g of 1-(2-O-(tert-butyldimethylsilyl)-β-D-erythro-pentofuran-3-ulosyl)uracil in 15 ml of tetrahydrofuran was added dropwise over about 30 minutes to the mixture by means of a cannula. After 150 minutes, 4.1 ml of acetic acid were added to the reaction mixture, and the resultant mixture was then heated to room temperature. The mixture was subjected to liquid separation using 500 ml of ethyl acetate and 300 ml of water. After the resultant organic layer was washed with 300 ml of water and 100 ml saturated saline, it was dried over anhydrous sodium sulfate. After the drying, the solvent was distilled off under reduced pressure, and the residue was purified by column chromatography on silica gel (hexane:ethyl acetate=2:1–3:2), thereby obtaining 2.05 g (yield: 83%) of 1-(2-O-(tert-butyldimethylsilyl)-3-C-triisopropylsilylethynyl-β-D-ribofuranosyl)uracil as a white foamy substance.

EI-MS: m/z (538($M^+$), 523($M^+$−Me), 495($M^+$−iPr), 481 ($M^+$−tBu).

$^1$H-NMR (DMSO-$d_6$) δ: 9.32(brs,1H), 8.01(d,1H), 5.90 (d,1H,J=7.3 Hz), 5.73(s,1H), 5.72(d,1H), 5.06(t,1H), 4.37 (d,1H,J=7.3 Hz), 3.96(brs,1H), 3.68–3.80(m,2H), 1.06(m, 21H), 0.81(s,9H), 0.10(s,3H), −0.04(s,3H).

Added to 2.0 g of 1-(2-O-(tert-butyldimethylsilyl)-3-C-triisopropylsilylethynyl-β-D-ribofuranosyl)uracil obtained above were 50 of a 2.6% (w/v) hydrochloric acid/methanol solution, and the mixture was stirred at room temperature. After 180 minutes, the solvent was distilled off under reduced pressure, and the residue was azeotropically distilled with ethanol, purified by column chromatography on covered silica gel (chloroform:methanol=50:1–15:1) and then suspended in hexane. The suspension was filtered to obtain 1.4 g (yield: 89%) of the title compound as a white powdered substance.

EI-MS: m/z 424($M^+$), 381($M^+$−iPr).

$^1$H-NMR (DMSO-$d_6$) δ: 9.35(brs,1H), 7.90(d,1H,J=8.1 Hz), 5.87(s,1H), 5.86(d,1H), 5.78(d,1H,J=6.1 Hz), 5.64(d, 1H,J=8.1 Hz), 4.95(t,1H), 4.12(t,1H,J=6.1 Hz), 3.89(t,1H), 3.73(m,2H), 1.06(s,21H).

Example 36

Synthesis of 1-(3-C-triphenylsilylethynyl-β-D-ribofuranosyl)uracil (Compound 38)

After 6.6 g of cerium chloride heptahydrate were dried at 140° C. for 7 hours under reduced pressure, its pressure was returned to ordinary pressure while introducing argon gas. While cooling with ice water and stirring vigrously, 21 ml of tetrahydrofuran were added at once to the cerium chloride, and the mixture was stirred overnight at room temperature.

After 5 g of triphenylsilylacetylene were added to 12 ml of tetrahydrofuran, and the mixture was cooled to −78° C. in an argon atmosphere, 10.5 ml of a 1.68M n-butyllithium/n-hexane solution were added dropwise over 10 minutes. As a result, the solution was solidified, and so the solid was gradually heated to 0° C. at which a solution was provided. This solution was stirred further for 30 minutes and added dropwise over about 30 minutes to the cerium chloride suspension cooled to −78° C. by means of a cannula. After completion of the drop addition, the mixture was stirred further for 60 minutes. A solution of 1.04 g of 1-(2-O-(tert-butyldimethylsilyl)-β-D-erythro-pentofuran-3-ulosyl)uracil in 6 ml of tetrahydrofuran was added dropwise over about 15 minutes to the mixture by means of the cannula. After 60 minutes, 2.7 ml of acetic acid were added to the reaction mixture, and the resultant mixture was then heated to room temperature. The mixture was subjected to liquid separation using 300 ml of ethyl acetate and 150 ml of water. After the resultant organic layer was washed with 150 ml of water and 150 ml of saturated saline, it was dried over anhydrous sodium sulfate. After the drying, the solvent was distilled off under reduced pressure, and the residue was purified by column chromatography on silica gel (chloroform:methanol=25:1), thereby obtaining 1.3 g (yield: 72%) of 1-(2-O-(tert-butyldimethylsilyl)-3-C-triphenylsilylethynyl-β-D-ribofuranosyl)uracil was a white foamy substance.

EI-MS: m/z 583($M^+$−tBu).

$^1$H-NMR (DMSO-$d_6$) δ: 9.31(brs,1H), 8.07(d,1H,J=8.1 Hz), 7.62(d,6H), 7.40–7.50(m,9H), 6.12(s,1H), 5.96(d,1H, J=7.5 Hz), 5.68(dd,1H,J=8.1 Hz), 5.35(t,1H), 4.50(d,1H,J= 7.5 Hz), 3.74–3.83(m,2H), 0.73(s,9H), −0.08(s,3H), −0.14 (s,3H).

Added to 1.3 g of 1-(2-O-(tert-butyldimethylsilyl)-3-C-triphenylsilylethynyl-β-D-ribofuranosyl)uracil obtain above were 30 ml of a 2.6% (w/v) hydrochloric acid/methanol solution, and the mixture was stirred at room temperature. After 110 minutes, the solvent was distilled off under reduced pressure, and the residue was then azeotropically distilled with ethanol, purified by column chromatography on covered silica gel (chloroform:methanol=20:1–15:1) and then suspended in hexane. The suspension was filtered to obtain 940 mg (yield: 86%) of the title compound as a pale-yellow powdered substance.

mp: 114°–116° C.

EI-MS: m/z 526($M^+$), 449($M^+$−Ph).

$^1$H-NMR (DMSO-$d_6$) δ: 9.37(brs,1H), 7.96(d,1H,J=8.1 Hz), 7.62(d,6H), 7.42–7.51(m,9H), 6.23(s,1H), 5.98(d,1H), 5.87(d,1H,J=6.9 Hz), 5.48(dd,1H,J=8.1 Hz), 5.19(t,1H), 4.33(t,1H,J=6.9 Hz), 4.01(t,1H), 3.74–3.85(m,2H).

Test Example 1

Survival effect against murine leukemia P388:

Murine Leukemia P388 cells ($1\times10^6$ cells) were implanted intraperitoneally in three female CDFI mice (aged 8 weeks) per group. On the day subsequent to the implantation and the fifth day, test compounds at varied concentrations were administered intraperitoneally to their corresponding groups of mice. Average survival days of each group were determined to find a survival rate (T/C, %) in accordance with the following equation. The results are shown in Table 1.

TABLE 1

$$\text{Survival rate } (T/C, \%) = \frac{\text{Average survival days of the treated group}}{\text{Average survival days of the control group}} \times 100$$

| Compound | Dose (mg/kg) | T/C (%) |
|---|---|---|
| Compound 2 | 3 | 206 |
| | 1 | 211 |
| Compound 7 | 3 | 150 |
| | 1 | 144 |

Test Example 2

Cytotoxicity:

Human KB cells were spread in a proportion of $1\times10^5$ cells/well on a 96-well plate. After a compound according to the present invention was dissolved in purified water, the solution was diluted to various concentrations with an RPMI 1640 medium and then added to each well, thereby conducting culture. After incubating at 37° C. for 3 days in a 5% $CO_2$-incubator, the number of cells was counted by an MTT method.

The cytotoxicity of each of the compounds tested was expressed by a concentration ($IC_{50}$) of the compound at which the number of cells was decreased by 50% compared with a control. The results are shown in Table 2.

TABLE 2

| Compound No. | $IC_{50}$ (μg/ml) |
|---|---|
| Compound 7 | 0.0077 |
| Compound 35 | 0.0078 |
| Comparative compound 1* | >100 |

*Comparative compound 1: 1-(3-C-ethyl-β-D-ribofuranosyl)uracil.

As apparent from the results, the compounds according to the present invention exhibited extremely strong cytotoxic activities compared with the already-known compound, 1-(3-C-ethyl-β-D-ribofuranosyl)uracil.

Preparation Examples using the compounds according to the present invention will hereinafter be described.

Preparation Example 1

Capsule preparation

A capsule preparation was formulated in accordance with the following formulation and a method known per se in the art.

| | |
|---|---|
| Compound 2 | 200 mg |
| Lactose | 30 mg |
| Corn starch | 50 mg |
| Crystalline cellulose | 10 mg |
| Magnesium stearate | 3 mg |
| One capsule contained | 293 mg. |

Preparation Example 2

Tablet preparation

A tablet preparation was formulated in accordance with the following formulation and a method known per se in the art.

| | |
|---|---|
| Compound 7 | 100 mg |
| Lactose | 47 mg |
| Corn starch | 50 mg |
| Crystalline cellulose | 50 mg |
| Hydroxypropylcellulose | 15 mg |
| Talc | 2 mg |
| Magnesium stearate | 2 mg |
| Ethylcellulose | 30 mg |
| Unsaturated fatty acid glyceride | 2 mg |
| Titanium dioxide | 2 mg |
| One tablet contained | 300 mg. |

Preparation Example 3

Granule preparation

A granule preparation was formulated in accordance with the following formulation and a method known per se in the art.

| | |
|---|---|
| Compound 14 | 200 mg |
| Mannitol | 540 mg |
| Corn starch | 100 mg |
| Crystalline cellulose | 100 mg |
| Hydroxypropylcellulose | 50 mg |
| Talc | 10 mg |
| One wrapper contained | 1000 mg. |

Preparation Example 4

Fine granule preparation

A fine granule preparation was formulated in accordance with the following formulation and a method known per se in the art.

| | |
|---|---|
| Compound 35 | 200 mg |
| Mannitol | 520 mg |
| Corn starch | 100 mg |
| Crystalline cellulose | 100 mg |
| Hydroxypropylcellulose | 70 mg |
| Talc | 10 mg |
| One wrapper contained | 1000 mg. |

Preparation Example 5

Injection preparation

An injection preparation was formulated in accordance with the following formulation and a method known per se in the art.

| | |
|---|---|
| Compound 4 | 100 mg |
| Distilled water for injection | Proper amount |
| One vial contained | 2 ml. |

Preparation Example 6

Suppository preparation

A suppository preparation was formulated in accordance with the following formulation and a method known per se in the art.

| | |
|---|---|
| Compound 10 | 200 mg |
| Witepaol S-55 (mixture of mono-, di- and triglycerides of saturated fatty acids from lauric acid to stearic acid, product of Dynamite Nobel Co.) | 1300 mg |
| One preparation contained | 1500 mg. |

INDUSTRIAL APPLICABILITY

The 3'-substituted nucleoside derivatives according to the present invention have an excellent antitumor activity and hence permit treatment for and prevention of cancers by administering them in various forms.

We claim:

1. A 3'-substituted nucleoside derivative represented by general formula (1), or a pharmaceutically acceptable salt thereof:

(1)

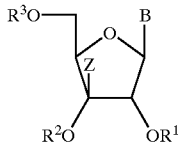

wherein B represents a nucleic acid base which may have a substituent, wherein Z represents:

[(i)] a lower alkynyl or lower alkenyl group which may be substituted by a group represented by general formula (2):

(2)

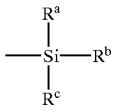

in which $R^a$, $R^b$ and $R^c$ may be the same or different from one another and individually represent a lower alkyl group or a phenyl group, [or (ii) an oxiranyl group which may be substituted by at least one lower alkyl group,]

wherein $R^1$ and $R^2$ individually represent a hydrogen atom or an [ester-forming residue capable of easily being removed in a living body] *aliphatic acyl group which may be substituted or an aromatic acyl group which may be substituted*, and $R^3$ is a hydrogen atom, a [mono- or polyphosphoric] *mono-, di- or tri-phosphoric* acid residue, or an [ester-forming residue capable of easily being removed in a living body] *aliphatic acyl group which may be substituted or an aromatic acyl group which may be substituted*, with the proviso that Z is in a cis configuration with respect to B.

2. The 3'-substituted nucleoside derivative or the pharmaceutically acceptable salt thereof according to claim 1, wherein B is [cytosine, thymine, uracil, adenine, guanine, 5-fluorocytosine, 5-fluorouracil, $N^6$-benzoyladenine, $N^2$-acetylguanine or 2-chloroadenine] *selected from the group consisting of 1-cytosinyl, 1-thyminyl, 1-uracilyl, 9-adeninyl, 9-guaninyl, 5-fluoro-1-cytosinyl, 5-fluoro-1-uracilyl, $N^6$-Benzoyl-9-adeninyl, $N^2$-acetyl-9-guaninyl and 2-chloro-9-adeninyl.*

3. The 3'-substituted nucleoside derivative or the pharmaceutically acceptable salt thereof according to claim 1, wherein B is [cytosine, uracil, adenine, 5-fluorocytosine or 5-fluorouracil] *selected from the group consisting of 1-cytosinyl, 1-uracilyl, 9-adeninyl, 5-fluoro-1-cytosinyl and 5-fluoro-1-uracilyl.*

4. The 3'-substituted nucleoside derivative or the pharmaceutically acceptable salt thereof according to any one of claims 1–3, wherein Z is a lower alkynyl or lower alkenyl group which may be substituted by a group represented by the general formula (2):

(2)

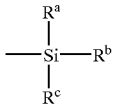

in which $R^a$, $R^b$ and $R^c$ may be the same or different from one another and individually represent a lower alkyl group or a phenyl group.

5. The 3'-substituted nucleoside derivative or the pharmaceutically acceptable salt thereof according to claim 4, wherein the group represented by the general formula (2) is a trimethylsilyl, triethylsilyl, triisopropylsilyl or triphenylsilyl group.

6. The 3'-substituted nucleoside derivative or the pharmaceutically acceptable salt thereof according to any one of claims 1–3, wherein Z is an ethynyl, propynyl, butynyl, ethenyl, trimethylsilylethynyl, triethylsilylethynyl, triisopropylsilylethynyl or triphenylsilylethynyl group.

7. The 3'-substituted nucleoside derivative or the pharmaceutically acceptable salt thereof according to any one of claims 1, 2 or 3, wherein $R^1$ and $R^2$ are hydrogen atoms, and $R^3$ is a hydrogen atom, or a [mono- or polyphosphoric] *mono-, di-or tri-phosphoric* acid residue.

8. The 3'-substituted nucleoside derivative or the pharmaceutically acceptable salt thereof according to any one of claims 1, 2 or 3 wherein $R^1$ and $R^2$ are hydrogen atoms, and $R^3$ is a hydrogen atom, or a monophosphate, diphosphate or triphosphate group.

9. The 3'-substituted nucleoside derivative or the pharmaceutically acceptable salt thereof according to any one of claims 1, 2 or 3 wherein [the ester-forming residues of] $R^1$, $R^2$ and $R^3$ are *said aliphatic* acyl [groups] *group or said aromatic acyl group.*

10. The 3'-substituted nucleoside derivative or the pharmaceutically acceptable salt thereof according to claim 1, wherein B is [cytosine, thymine, uracil, adenine, guanine, 5-fluorocytosine, 5-fluorouracil, $N^6$-benzoyladenine, $N^2$-acetylguanine or 2-chloroadenine] *selected from the group consisting of 1-cytosinyl, 1-thyminyl, 1-uracilyl, 9-adeninyl, 9-guaninyl, 5-fluoro-1-cytosinyl, 5-fluoro-1-uracilyl, $N^6$-benzoyl-9-adeninyl, $N^2$-acetyl-9-guaninyl and 2-chloro-9-adeninyl*, Z is a lower alkynyl or lower alkenyl group which may be substituted by a group represented by the general formula (2):

(2)

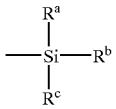

in which $R^a$, $R^b$ and $R^c$ may be the same or different from one another and individually represent a lower alkyl group or a phenyl group, $R^1$ and $R^2$ are hydrogen atoms, and $R^3$ is a hydrogen atom, or a [mono- or polyphosphoric] *mono-, di- or tri-phosphoric* acid residue.

11. The 3'-substituted nucleoside derivative or the pharmaceutically acceptable salt thereof according to claim 1, wherein B is [cytosine, uracil, adenine, 5-fluorocytosine or 5-fluorouracil] *selected from the group consisting of 1-cytosinyl, 1-uracilyl, 9-adeninyl, 5-fluoro-1-cytosinyl and 5-fluoro-1-uracilyl*, Z is an ethynyl, propynyl, butynyl, ethenyl, trimethylsilylethynyl, triethylsilyl-ethynyl, triisopropylsilylethynyl or triphenylsilylethynyl group, $R^1$ and $R^2$ are hydrogen atoms, and $R^3$ is a hydrogen atom or a diphosphate group.

12. The 3'-substituted nucleoside derivative or the pharmaceutically acceptable salt thereof according to claim 1, wherein B is [cytosine or uracil] *1-cytosinyl or 1-uracilyl*, Z is an ethynyl or trimethylsilylethynyl group, and $R^1$, $R^2$ and $R^3$ are hydrogen atoms.

13. A pharmaceutical composition comprising the 3'-substituted nucleoside derivative or the pharmaceutically acceptable salt thereof according to any one of claims 1, 2, 3, 10, 11 or 12 and a pharmaceutical carrier.

14. A method of treating a cancer of a mammal in need thereof, which comprises administering an effective amount of the 3'-substituted nucleoside derivative or the pharmaceutically acceptable salt thereof according to any one of claim 1, 2, 3, 10, 11 or 12 to the mammal.

15. A process for the preparation of a 3'-substituted nucleoside derivative represented by general formula (1), or a pharmaceutically acceptable salt thereof:

(1)

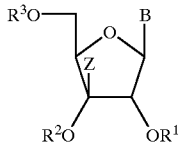

wherein B represents a nucleic acid base which may have a substituent, wherein Z represents:

[(i)] a lower alkynyl or lower alkenyl group which may be substituted by a group represented by general formula (2):

(2)

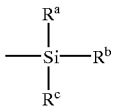

in which $R^a$, $R^b$ and $R^c$ may be the same or different from one another and individually represent a lower alkyl group or a phenyl group, [or (ii) an oxiranyl group which may be substituted by at least one lower alkyl group,]

wherein $R^1$ and $R^2$ individually represent a hydrogen atom or an [ester-forming residue capable of easily being removed in a living body] *aliphatic acyl group which may be substituted or an aromatic acyl group which may be substituted*, and $R^3$ is a hydrogen atom, a [mono- or polyphosphoric] *mono-, di- or tri-phosphoric* acid residue, or an [ester-forming residue capable of easily being removed in a living body] *aliphatic acyl group which may be substituted or an aromatic acyl group which may be substituted*, with the proviso that Z is in a cis configuration with respect to B, which comprises the step of:

reacting a sugar derivative represented by general formula (3):

(3)

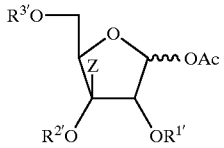

wherein $R^{1'}$, $R^{2'}$ and $R^{3'}$ mean individually a protecting group for a hydroxyl group, Ac represents an acetyl group, and Z has the same meaning as defined above, with a nucleic acid derivative represented by general formula (4):

B—Y (4)

wherein B has the same meaning as defined above, and Y is a silyl protecting group, *wherein said reacting occurs in the presence of a Lewis acid in a nonpolar solvent*.

16. The process of claim 15, wherein the process [additionally] *further* comprises the step of [eliminating] *removing* the protecting group for at least one of the hydroxyl groups, and subsequently introducing an [ester capable of easily being removed in a living body] *aliphatic acyl group which may be substituted or an aromatic acyl group which may be substituted* or a phosphoric [ester] *ester(s)*.

17. A process for the preparation of a 3'-substituted nucleoside derivative represented by general formula (1), or a pharmaceutically acceptable salt thereof:

(1)

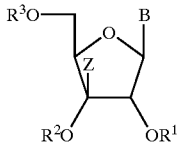

wherein B represents a nucleic acid base which may have a substituent, wherein Z represents:

[(i)] a lower alkynyl or lower alkenyl group which may be substituted by a group represented by general formula (2):

(2)

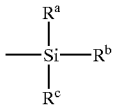

in which $R^a$, $R^b$ and $R^c$ may be the same or different from one another and individually represent a lower alkyl group or a phenyl group, [or (ii) an oxiranyl group which may be substituted by at least one lower alkyl group,]

wherein $R^1$ and $R^2$ individually represent a hydrogen atom or an [ester-forming residue capable of easily being removed in a living body] *aliphatic acyl group which may be substituted or an aromatic acyl group which may be substituted*, and $R^3$ is a hydrogen atom, a [mono- or polyphosphoric] *mono-, di- or tri-phosphoric* acid residue, or an [ester-forming residue capable of easily being removed in a living body] *aliphatic acyl group which may be substituted or an aromatic acyl group which may be substituted*, with the proviso that Z is in a cis configuration with respect to B, which comprises the steps of:

(A) partially hydrolyzing a compound represented by general formula (5):

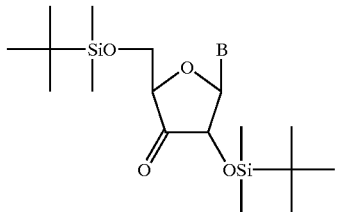

(5)

wherein B has the same meaning as defined above, to form a compound represented by general formula (6):

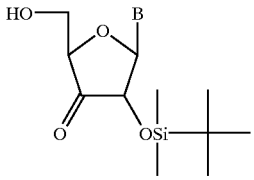

(6)

wherein B has the same meaning as defined above, (B) reacting the resulting compound represented by general formula (6) with a compound represented by formula:

z—x wherein Z has the same meaning as defined above, and X represents a hydrogen or halogen atom, or MgBr, *wherein when X represents a hydrogen or halogen atom, said reacting occurs in the presence of n-butyllithium in tetrahydrofuran; and wherein when X represents MgBr, said reacting occurs in tetrahydrofuran,* to form a compound represented by general formula (7):

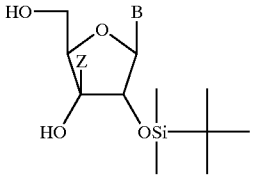

(7)

wherein B and Z have the same meaning as defined above, and (C) hydrolyzing the resulting compound represented by general formula (7) *to give rise to a compound represented by general formula* (*1*).

18. The process of claim 17, wherein the process [additionally] *further* comprises the step of forming [a phosphoric ester] *an ester*(*s*) of (*i*) *a phosphoric acid forming residue;* (*ii*) an [ester capable of easily being removed in a living body] *aliphatic acyl group which may be substituted, or* (*iii*) *an aromatic acyl group which may be substituted*, with at least one of the hydroxyl groups.

*19. 1-(3-C-ethynyl-β-D-ribofuranosyl) cytosine or a pharmaceutically acceptable salt, or hydrate thereof.*

*20. A pharmaceutical composition comprising the compound as defined in claim 19 and a pharmaceutically acceptable carrier.*

*21. A method of treating a cancer of a mammal in need thereof, which comprises administering an effective amount of the compound as defined in claim 19 to the mammal.*

*22. The method according to claim 21, wherein said mammal is a human.*

* * * * *